(12) United States Patent
Taylor et al.

(10) Patent No.: US 11,707,263 B2
(45) Date of Patent: Jul. 25, 2023

(54) TISSUE RETRIEVAL SYSTEM WITH RETENTION FEATURES

(71) Applicant: Applied Medical Resources Corporation, Rancho Santa Margarita, CA (US)

(72) Inventors: Scott V. Taylor, Rancho Santa Margarita, CA (US); Quoc P. Tran, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 818 days.

(21) Appl. No.: 16/685,634

(22) Filed: Nov. 15, 2019

(65) Prior Publication Data

US 2020/0155133 A1    May 21, 2020

Related U.S. Application Data

(60) Provisional application No. 62/768,254, filed on Nov. 16, 2018.

(51) Int. Cl.
*A61B 17/00* (2006.01)
*A61B 17/34* (2006.01)

(52) U.S. Cl.
CPC .... *A61B 17/00234* (2013.01); *A61B 17/3423* (2013.01); *A61B 2017/00287* (2013.01);
(Continued)

(58) Field of Classification Search
CPC .......... A61B 17/00234; A61B 17/3423; A61B 2017/00287; A61B 2017/00407;
(Continued)

(56) References Cited

U.S. PATENT DOCUMENTS 30,471 A    10/1860 Dudley
1,609,014 A    11/1926 Dowd
(Continued)

FOREIGN PATENT DOCUMENTS

DE    25796    1/1884
DE    4216165 A1    11/1992
(Continued)

OTHER PUBLICATIONS

U.S. Pat. No. 5,853,374, filed Oct. 11, 1995 entitled Tissue Retrieval System and associated file history.
(Continued)

*Primary Examiner* — Mohamed G Gabr
(74) *Attorney, Agent, or Firm* — John F. Heal

(57) ABSTRACT

A tissue retrieval system including a tissue retrieval bag deployable from an introducer and suspended in an open configuration by support arms can include retention features to prevent inadvertent movement of the tissue retrieval bag relative to the support arms. The support arms can include protruding domes, folds, or curls to restrict sliding of the tissue retrieval bag relative to the support arms. Alternately, tension can be maintained in a cord loop coupled to an opening of the tissue retrieval bag to prevent the tissue retrieval bag from inadvertently sliding relative to the support arms.

11 Claims, 22 Drawing Sheets

(52) U.S. Cl.
CPC .............. *A61B 2017/00407* (2013.01); *A61B 2017/00858* (2013.01); *A61B 2017/00867* (2013.01)

(58) Field of Classification Search
CPC .... A61B 2017/0042; A61B 2017/0046; A61B 2017/00858; A61B 2017/00867; A61B 2090/034; A61B 2090/037
See application file for complete search history.

(56) References Cited

U.S. PATENT DOCUMENTS

| | | |
|---|---|---|
| 3,476,114 A | 11/1969 | Shannon et al. |
| 3,476,115 A | 11/1969 | Graeff et al. |
| 4,287,807 A | 9/1981 | Pacharis et al. |
| 4,428,375 A | 1/1984 | Ellman |
| 4,732,150 A | 3/1988 | Keener Jr. |
| 4,741,335 A | 5/1988 | Okada |
| 4,991,593 A | 2/1991 | LeVahn |
| 5,037,379 A | 8/1991 | Clayman et al. |
| 5,074,867 A | 12/1991 | Wilk |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,195,507 A | 3/1993 | Bilweis |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,279,548 A | 1/1994 | Essig et al. |
| 5,308,327 A | 5/1994 | Heaven et al. |
| 5,312,416 A | 5/1994 | Spaeth et al. |
| 5,336,227 A | 8/1994 | Nakao et al. |
| 5,337,754 A | 8/1994 | Heaven et al. |
| 5,341,815 A | 8/1994 | Cotone et al. |
| 5,352,184 A | 10/1994 | Goldberg et al. |
| 5,354,303 A | 10/1994 | Spaeth et al. |
| 5,366,460 A | 11/1994 | Eberbach |
| 5,368,597 A | 11/1994 | Pagedas |
| 5,417,684 A | 5/1995 | Jackson et al. |
| 5,417,697 A | 5/1995 | Wilk et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| RE35,164 E | 3/1996 | Kindberg et al. |
| 5,509,923 A | 4/1996 | Middleman et al. |
| 5,524,633 A | 6/1996 | Heaven et al. |
| 5,535,759 A | 7/1996 | Wilk |
| 5,601,572 A | 2/1997 | Middleman et al. |
| 5,611,803 A | 3/1997 | Heaven et al. |
| 5,613,973 A | 3/1997 | Jackson et al. |
| 5,632,746 A | 5/1997 | Middleman et al. |
| 5,643,283 A | 7/1997 | Younker |
| 5,647,372 A | 7/1997 | Tovey et al. |
| 5,655,657 A | 8/1997 | Roshdy |
| 5,656,012 A | 8/1997 | Sienkiewicz |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,749,879 A | 5/1998 | Middleman et al. |
| 5,755,724 A | 5/1998 | Yoon |
| 5,759,187 A | 6/1998 | Nakao et al. |
| 5,779,716 A | 7/1998 | Cano et al. |
| 5,782,839 A | 7/1998 | Hart et al. |
| 5,785,677 A | 7/1998 | Auweiler |
| 5,788,709 A | 8/1998 | Riek et al. |
| 5,809,621 A | 9/1998 | McCree et al. |
| 5,820,628 A | 10/1998 | Middleman et al. |
| 5,836,953 A | 11/1998 | Yoon |
| 5,853,374 A | 12/1998 | Hart et al. |
| 5,904,690 A | 5/1999 | Middleman et al. |
| 5,947,978 A | 9/1999 | Holsinger |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,015,415 A | 1/2000 | Avellanet |
| 6,019,770 A | 2/2000 | Christoudias |
| 6,059,793 A | 5/2000 | Pagedas |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,350,267 B1 | 2/2002 | Stefanchik |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,575,988 B2 | 6/2003 | Rousseau |
| 6,805,699 B2 | 10/2004 | Shimm |
| 6,814,739 B2 | 11/2004 | Secrest et al. |
| 6,958,069 B2 | 10/2005 | Shipp et al. |
| 6,986,774 B2 | 1/2006 | Middleman et al. |
| 7,041,055 B2 | 5/2006 | Young et al. |
| 7,115,125 B2 | 10/2006 | Nakao et al. |
| 7,270,663 B2 | 9/2007 | Nakao |
| 7,547,310 B2 | 6/2009 | Whitfield |
| 7,618,437 B2 | 11/2009 | Nakao |
| 7,670,346 B2 | 3/2010 | Whitfield |
| 8,062,306 B2 | 11/2011 | Nobis et al. |
| 8,409,112 B2 * | 4/2013 | Wynne .............. A61B 10/0096 606/205 |
| 2003/0100919 A1 | 5/2003 | Hopkins et al. |
| 2004/0087969 A1 | 5/2004 | Kayan et al. |
| 2004/0097960 A1 | 5/2004 | Terachi et al. |
| 2004/0138587 A1 | 7/2004 | Lyons, IV |
| 2004/0158261 A1 | 8/2004 | Vu |
| 2004/0193184 A1 | 9/2004 | Laufer et al. |
| 2004/0254573 A1 | 12/2004 | Dycus et al. |
| 2005/0165411 A1 | 7/2005 | Orban, III |
| 2005/0267489 A1 | 12/2005 | Secrest et al. |
| 2005/0267492 A1 | 12/2005 | Poncet et al. |
| 2006/0052799 A1 | 3/2006 | Middleman et al. |
| 2006/0074406 A1 | 4/2006 | Cooper et al. |
| 2006/0173468 A1 | 8/2006 | Simmon et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0276805 A1 | 12/2006 | Yu |
| 2007/0088370 A1 | 4/2007 | Kahle et al. |
| 2008/0033451 A1 | 2/2008 | Rieber et al. |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2009/0043315 A1 | 2/2009 | Moon |
| 2009/0082779 A1 | 3/2009 | Nakao |
| 2009/0019251 A1 | 7/2009 | Bahney |
| 2009/0306683 A1 | 12/2009 | Zwolinski et al. |
| 2010/0076451 A1 | 3/2010 | Zwolinski et al. |
| 2010/0152609 A1 | 6/2010 | Zwolinski et al. |
| 2010/0152746 A1 | 6/2010 | Ceniccola et al. |
| 2011/0184433 A1 * | 7/2011 | Parihar ............ A61B 17/00234 606/114 |

FOREIGN PATENT DOCUMENTS

| | | |
|---|---|---|
| DE | 197 07 361 A1 | 8/1998 |
| EP | 499243 A1 | 8/1992 |
| EP | 0 947 166 A2 | 10/1999 |
| JP | 5-115493 A | 5/1993 |
| JP | 6-154161 A | 6/1994 |
| SU | 1537229 A1 | 1/1990 |
| WO | WO 1993/15671 A1 | 8/1993 |
| WO | WO 1993/24063 A1 | 12/1993 |

(56) References Cited

FOREIGN PATENT DOCUMENTS

| WO | WO 1994/13215 A2 | 6/1994 |
|----|------------------|--------|
| WO | WO 2003/105674 A2 | 12/2003 |
| WO | WO 2007/081601 A2 | 7/2007 |
| WO | WO 2011/090864 A2 | 7/2011 |

OTHER PUBLICATIONS

U.S. Appl. No. 11/549,701, filed Oct. 16, 2006, entitled "Laparoscopic Tissue Retrieval System" and associated file history.

U.S. Appl. No. 11/549,971, filed Oct. 16, 2006 entitled Tissue Retrieval System and associated file history.

U.S. Appl. No. 12/902,055, filed Oct. 11, 2010 entitled "Single Incision Laparoscopic Tissue Retrieval System" and associated file history.

U.S. Appl. No. 13/252,110, filed Oct. 3, 2011, entitled "Laparoscopic Tissue Retrieval System" and associated file history.

The International Bureau of WIPO, The International Preliminary Report on Patentability for International Application No. PCT/US2006/060007, entitled Device for Isolating and Removing Tissue from Body Cavity, dated Apr. 16, 2008, 8 pgs.

The International Bureau of WIPO, The International Preliminary Report on Patentability for International Application No. PCT/US2006/060022, entitled "Tissue Retrieval System," dated Apr. 16, 2008, 10 pgs.

European Patent Office, International Search Report and Written Opinion of the International Searching Authority for International Application No. PCT/US2006/060007, entitled Device for Isolating and Removing Tissue from Body Cavity, dated Feb. 22, 2007, 13 pgs.

European Patent Office, International Search Report and Written Opinion of the International Searching Authority for International Application No. PCT/US2006/060022, entitled "Tissue Retrieval System," dated Mar. 8, 2007, 17 pgs.

International Searching Authority, International Search Report and Written Opinion for International Application No. PCT/US2010/052190, entitled "Single Incision Laparoscopic Tissue Retrieval System", dated Jan. 25, 2011, 11 pgs.

International Searching Authority, International Search Report and Written Opinion for International Application No. PCT/US2011/054647, entitled "Laparoscopic Tissue Retrieval System", dated Feb. 21, 2012, 8 pgs.

The International Bureau of WIPO, The International Preliminary Report on Patentability for International Application No. PCT/US2010/052190, entitled "Single Incision Laparoscopic Tissue Retrieval System", dated Apr. 11, 2012, 5 pgs.

United States Surgical, Tyco Healthcare Group LP, Autosuture *Endo Catch* Single Use Specimen Retrieval Products, Frequently Asked Questions and Features and Benefits (web pages), 2004, 4 pgs.

United States Surgical, Tyco Healthcare Group LP, Autosuture* Endocatch* Gold 10 mm Single-Use Specimen Pouch, 10000-25912, Product Information Data Sheet, Feb. 2004, 2 pgs.

United States Surgical, Tyco Healthcare Group LP, Autosuture* Endocatch* II Single-Use Specimen Pouch, 10000-19724, Product Information Data Sheet, Aug. 2002, 2 pgs.

Conmed Corporation, EndoSurgery Products, Hand Held Laparoscopic Instruments, Product Descriptions (Web pages), 2004, 3 pgs.

Cook Group Inc., Cook Urological, Cook® Drainage Pouch Sets, Product Description (Web page), 2003, 1 pg.

Johnson & Johnson Gateway LLC, Ethicon Endo-Surgery Inc., Endoscopic Product Family, Endopouch Retriever Specimen Retrieval Bag, Product Description (Web Page), 2000-2005, 1 pg.

European Patent Office, International Search Report and Written Opinion of the International Searching Authority for International Application No. PCT/US2019/061788, entitled "Tissue Retrieval System with Retention Features," dated May 19, 2020, 10 pgs.

The International Bureau of WIPO, International Preliminary Report on Patentability for International Application No. PCT/US2019/061788, entitled "Tissue Retrieval System with Retention Features," dated May 27, 2021, 7 pgs.

\* cited by examiner

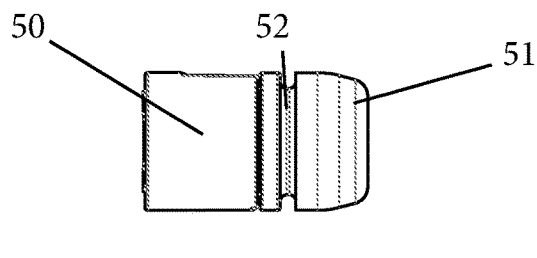
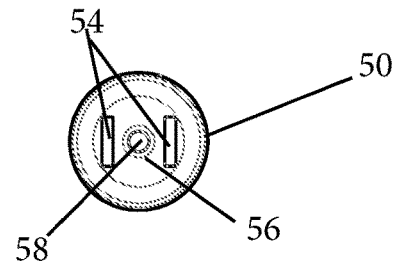
FIG. 8   FIG. 9
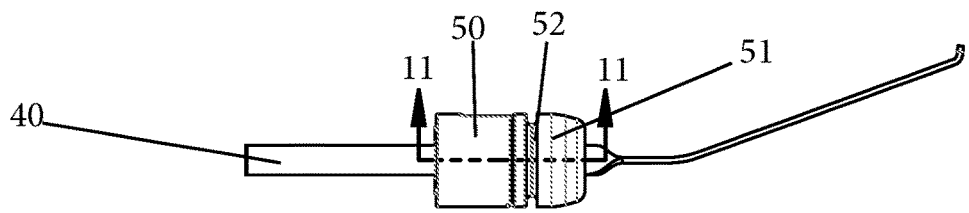
FIG. 10
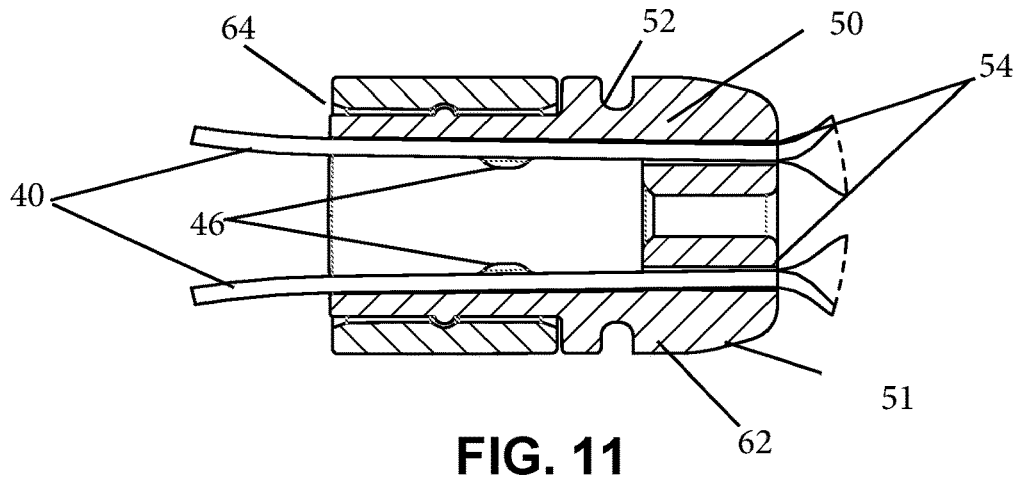
FIG. 11
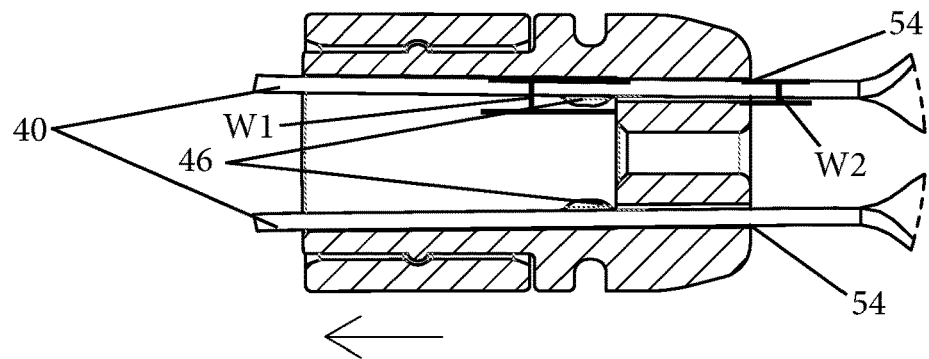
FIG. 12

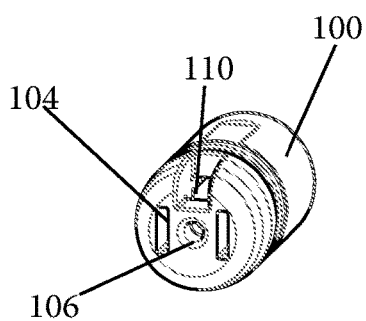
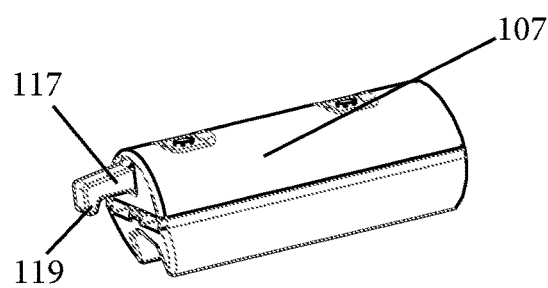
FIG. 13  FIG. 14
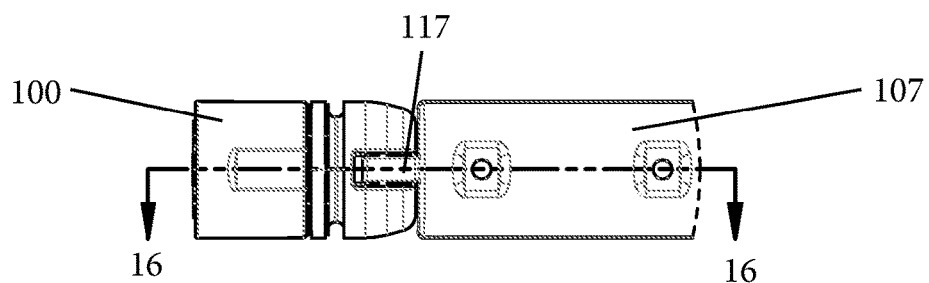
FIG. 15
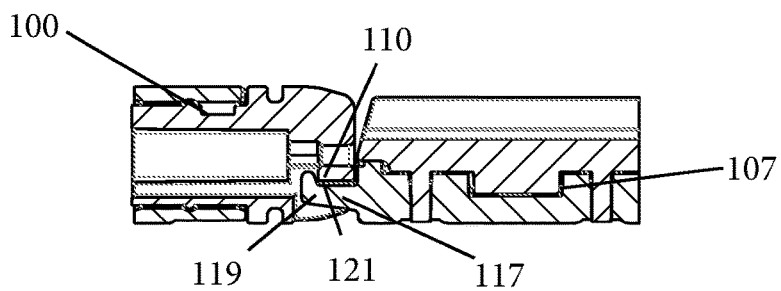
FIG. 16A
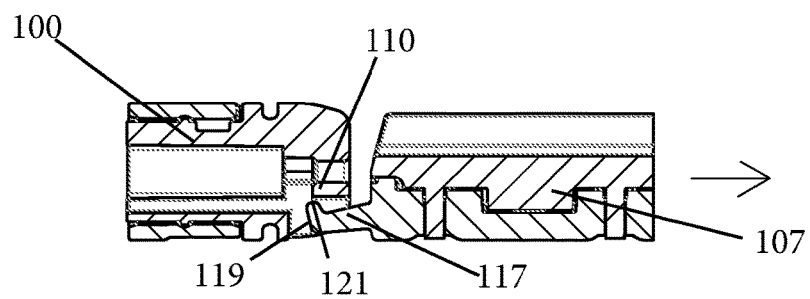
FIG. 16B

TISSUE RETRIEVAL SYSTEM WITH RETENTION FEATURES

CROSS-REFERENCE TO RELATED APPLICATIONS

This application claims priority to and benefit of U.S. Provisional Patent Application Ser. No. 62/768,254 entitled "Tissue Retrieval System with Retention Features" filed on Nov. 16, 2018 which is incorporated herein by reference in its entirety.

BACKGROUND OF THE INVENTION

Field of the Invention

The present application relates generally to apparatuses and methods for capturing and retrieving tissue from body cavities and in particular to a specimen retrieval bag device.

Description of the Related Art

Laparoscopic surgery is typically performed through trocars, which provide access across the abdominal wall and into the abdominal cavity. In some surgeries, tissue disposed within the abdominal cavity is cut and removed from the body. However, removal of such tissue from the body may prove difficult due to the limited confines inherent with laparoscopic surgery and the available laparoscopic surgical instruments. For example, to reduce the invasiveness to a patient, it can be desirable to introduce all of the surgical instruments through a single laparoscopic port having a relatively small size. Also, removed tissue may include an infected or cancerous mass or organ, as well as blood, bile and other liquids, all referred to herein as tissue, which may pose infection issues or other complications if left within the body.

It is desirable to grasp, capture, retain and enclose this tissue while in the body cavity, and then remove the enclosed tissue through the trocar or incision. Containment of the tissue as quickly as possible with minimal disturbance to the surgical site is also desirable. A generally compact and single unit device would also prove desirable as devices generally bulky and complicated have several shortcomings and lack optimal efficiency in particular with the limited space in operating rooms and access ports in the body cavity.

SUMMARY OF THE INVENTION

In certain embodiments, a tissue retrieval system is provided herein. The tissue retrieval system comprises a tubular introducer, an actuator, a pair of support arms, a guide bead, and a tissue retrieval bag. The tubular introducer has a proximal end and a distal end and a lumen extending between the proximal end and the distal end. The actuator is longitudinally slidable within the lumen of the introducer. The actuator has a proximal end and a distal end. The pair of support arms extends from the distal end of the actuator. The tissue retrieval bag is coupled to the guide bead and removably coupled to the support arms. The tissue retrieval bag is positionable within the lumen of the introducer in a stowed configuration and deployable by longitudinal movement of the actuator within the lumen of the introducer to an open configuration wherein the tissue retrieval bag is suspended from the support arms. The support arms comprise at least one retention dome sized and configured to maintain a position of the tissue retrieval bag relative to the support arms.

In certain embodiments, a tissue retrieval system is provided herein. The tissue retrieval system comprises a tubular introducer, an actuator, an actuator cap, a pair of support arms, a guide bead, and a tissue retrieval bag. The tubular introducer has a proximal end and a distal end and a lumen extending between the proximal end and the distal end. The actuator is longitudinally slidable within the lumen of the introducer. The actuator has a proximal end and a distal end. The actuator cap is positioned at a distal end of the actuator. The pair of support arms extend from the actuator cap. The tissue retrieval bag is coupled to the guide bead and removably coupled to the support arms. The tissue retrieval bag is positionable within the lumen of the introducer in a stowed configuration and deployable by longitudinal movement of the actuator within the lumen of the introducer to an open configuration wherein the tissue retrieval bag is suspended from the support arms. The actuator cap is releasably mateable with the guide bead to maintain a position of the tissue retrieval bag relative to the support arms.

In certain embodiments, a tissue retrieval system is provided herein. The tissue retrieval system comprises a tubular introducer, an actuator, a pair of support arms, a guide bead, a tissue retrieval bag, and a cord loop. The tubular introducer has a proximal end and a distal end and a lumen extending between the proximal end and the distal end. The actuator is longitudinally slidable within the lumen of the introducer. The actuator has a proximal end and a distal end. The actuator comprises a receiving channel adjacent the distal end. The pair of support arms extends from the distal end of the actuator. The tissue retrieval bag is coupled to the guide bead and removably coupled to the support arms. The tissue retrieval bag is positionable within the lumen of the introducer in a stowed configuration and deployable by longitudinal movement of the actuator within the lumen of the introducer to an open configuration wherein the tissue retrieval bag is suspended from the support arms. The cord loop is operably coupled to the tissue retrieval bag and cinchable to close the tissue retrieval bag from the open configuration. The cord loop is engaged with the receiving channel of the actuator to restrict movement of the cord loop to maintain a position of the tissue retrieval bag relative to the support arms.

BRIEF DESCRIPTION OF THE DRAWINGS

FIG. 8 is a side view of an embodiment of guide bead for the tissue retrieval system of FIG. 1;

FIG. 9 is a front view of the guide bead of FIG. 8;

FIG. 10 is a side view of the guide bead of FIG. 8 disposed on a support arm of the tissue retrieval system of FIG. 1;

FIG. 11 is a section view of the guide bead and support arms of the tissue retrieval system of FIG. 1 with the guide bead in a first position;

FIG. 12 is a section view of the guide bead and support arms of the tissue retrieval system of FIG. 1 with the guide bead in a second position FIG. 13 is a perspective view of an embodiment of guide bead for use in an embodiment of tissue retrieval system;

FIG. 14 is a perspective view of an embodiment of an actuator cap positioned on a distal end of the actuator for use with the guide bead of FIG. 13;

FIG. 15 is a bottom view of the guide bead and actuator cap of FIGS. 13 and 14;

FIG. 16A is a cross-sectional side view of the guide bead and actuator cap of FIGS. 13 and 14 in a coupled configuration;

FIG. 16B is a cross-sectional side view of the guide bead and actuator cap of FIGS. 13 and 14 in a decoupled configuration;

DETAILED DESCRIPTION OF THE INVENTION

Figure 1:
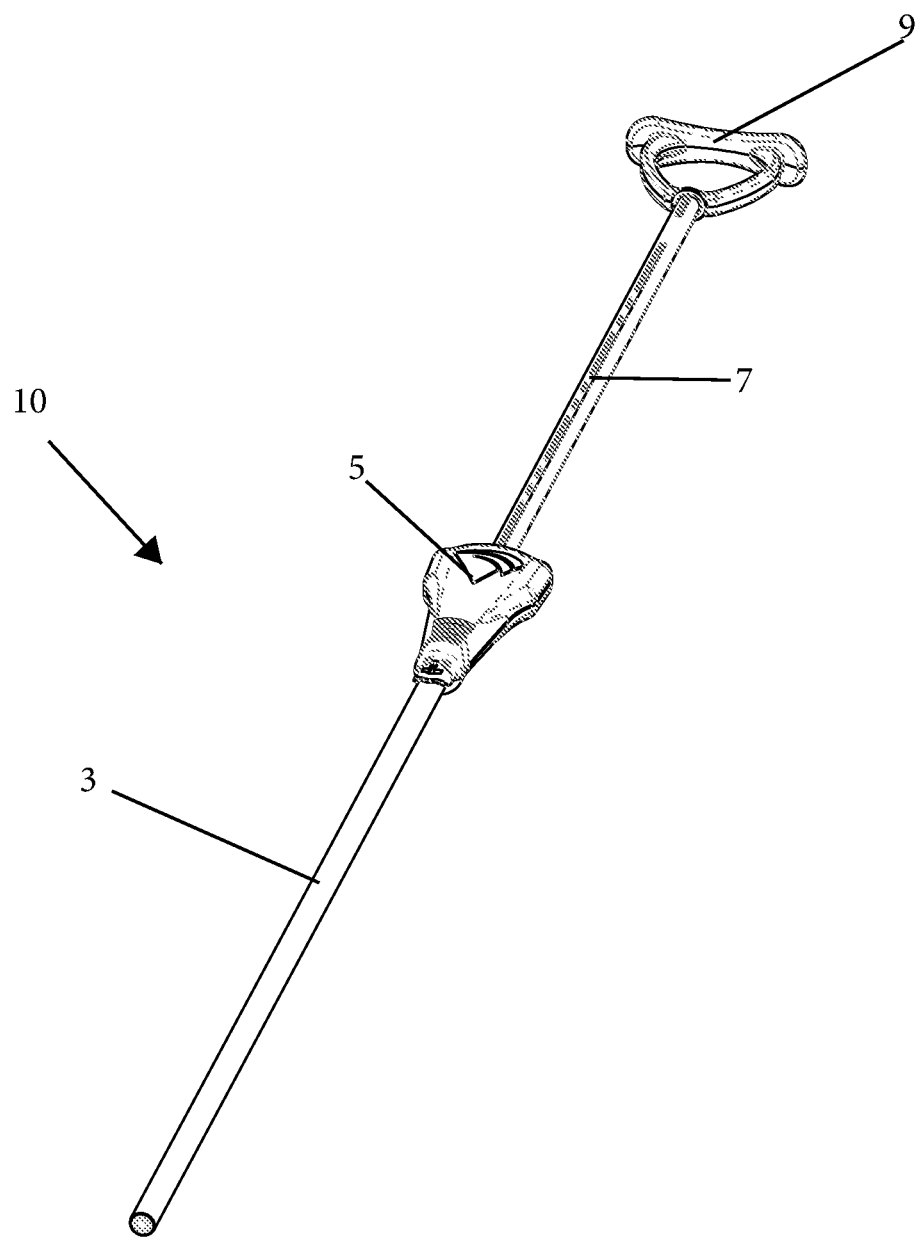
FIG. 1 is a perspective view of an embodiment of tissue retrieval system.

With reference to FIG. 1, an embodiment of tissue retrieval system 10 is illustrated. The illustrated tissue retrieval system can be used for containing and withdrawing excised tissue specimens from within a body cavity. For example, in some embodiments, the tissue retrieval system can be used to remove a patient's gallbladder from the patient's abdominal cavity. Thus, advantageously, the tissue retrieval systems discussed herein provide an easy to use tissue retrieval system which effectively contains excised tissue specimens to prevent loss or spillage of tissue specimens into a body cavity, and to protect the body wall access port site from contamination with the excised tissue specimens during withdrawal of the tissue specimens from within the body cavity. Certain aspects of tissue retrieval systems are described in U.S. Pat. No. 8,721,658, entitled "TISSUE RETRIEVAL SYSTEM," and U.S. Pat. No. 9,033,995, entitled "SINGLE INCISION LAPAROSCOPIC TISSUE RETRIEVAL SYSTEM," which are each incorporated by reference herein in their entireties.

With continued reference to FIG. 1, the tissue retrieval system 10 is illustrated in a non-deployed or non-activated initial condition. In the illustrated embodiment, the tissue retrieval system has an introducer 3 and an actuator or actuation rod 7. The introducer 3 in one aspect has a tubular configuration with a hollow lumen and a handle assembly 5 extending from a proximal end of the introducer 3. In some embodiments, the introducer 3 can be sized and configured for placement through a standard-size trocar. For example, it can be desirable that the introducer 3 can be sized as a 5 mm laparoscopic surgical instrument to be introduced through relatively small diameter trocars such as 5-7 mm trocars. In other embodiments, the introducer 3 can be sized as either a 10 mm, 12 mm, or 15 mm laparoscopic surgical instrument. In some embodiments, the introducer 3 can have a non-standard size for application at a specific location. In some embodiments, the tissue retrieval system 10 can include a relatively long introducer, such as, for example, a 45 cm long introducer 3 to improve access to the surgical site.

The handle assembly 5 of the illustrated embodiment can comprise a compact handle member that can be adapted for placement adjacent other surgical instruments in a single port laparoscopic surgical site. Thus, in some embodiments, the tissue retrieval system is adapted to be utilized during single incision laparoscopic procedures. In other embodiments, the handle assembly can include a pair of finger loops or grips formed with or otherwise coupled to the handle assembly 5 that can be utilized to hold or stabilize the introducer 3 as desired.

In the illustrated embodiment of tissue retrieval system 10, the introducer 3 has a proximal end and a distal end that are generally open, which can facilitate access to the hollow lumen. As illustrated, the actuator rod 7 extends into the hollow lumen from the open proximal end thereof, and at least a portion of the actuator rod 7 is slidably movable within the hollow lumen of the introducer 3. As further discussed with reference to FIGS. 2 and 3, with the tissue retrieval system 10 in the initial configuration, a tissue retrieval bag 20 in a stowed configuration can be positioned in the hollow lumen of the introducer 3. The actuator rod 7 in one aspect has a handle 9 extending from a proximal end thereof. The handle 9 provides a graspable portion of the device to control or facilitate movement of the actuator rod 7 relative to the introducer 3 between the initial condition of the tissue retrieval system 10 (illustrated in FIG. 1), and a deployed condition of the tissue retrieval system (illustrated in FIGS. 2-3).

Figure 2:
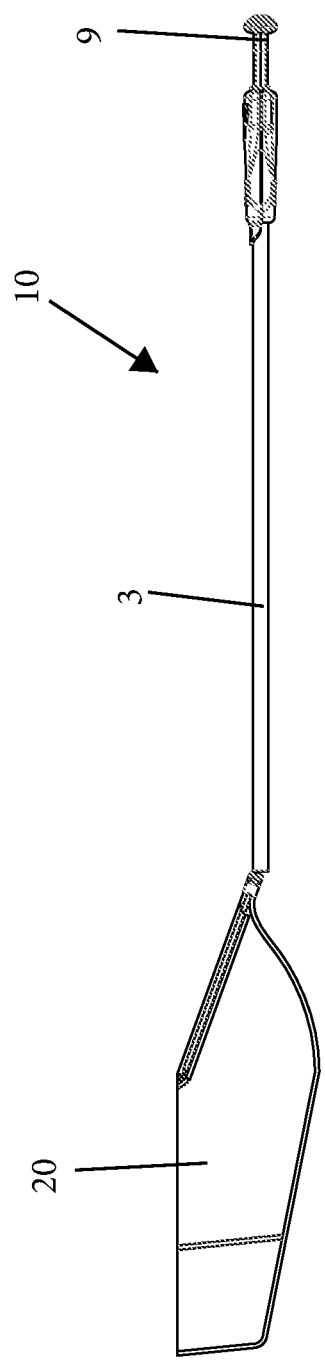
FIG. 2 is a side view of the tissue retrieval system of FIG. 1 with the retrieval bag deployed.
Figure 3:
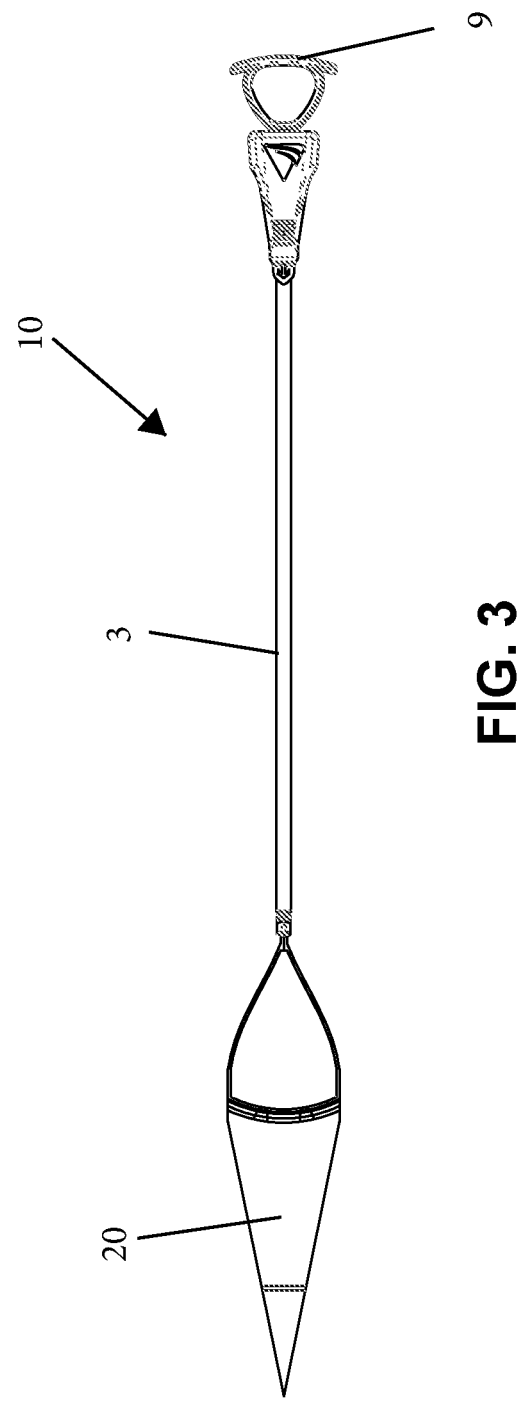
FIG. 3 is a top view of the tissue retrieval system of FIG. 1 with the retrieval bag deployed.

With reference to FIGS. 2 and 3, the tissue retrieval system can include a retrieval bag 20 that is deployable from the distal end of the introducer 3. The deployed retrieval bag 20 can be used as a receptacle for tissue specimens. After insertion of tissue specimens into the retrieval bag 20, the retrieval bag can then be cinched closed to prevent spillage of its contents and to prevent contamination of the body cavity and body cavity wall during withdrawal of the retrieval bag 20 from within the body cavity.

Figure 4:
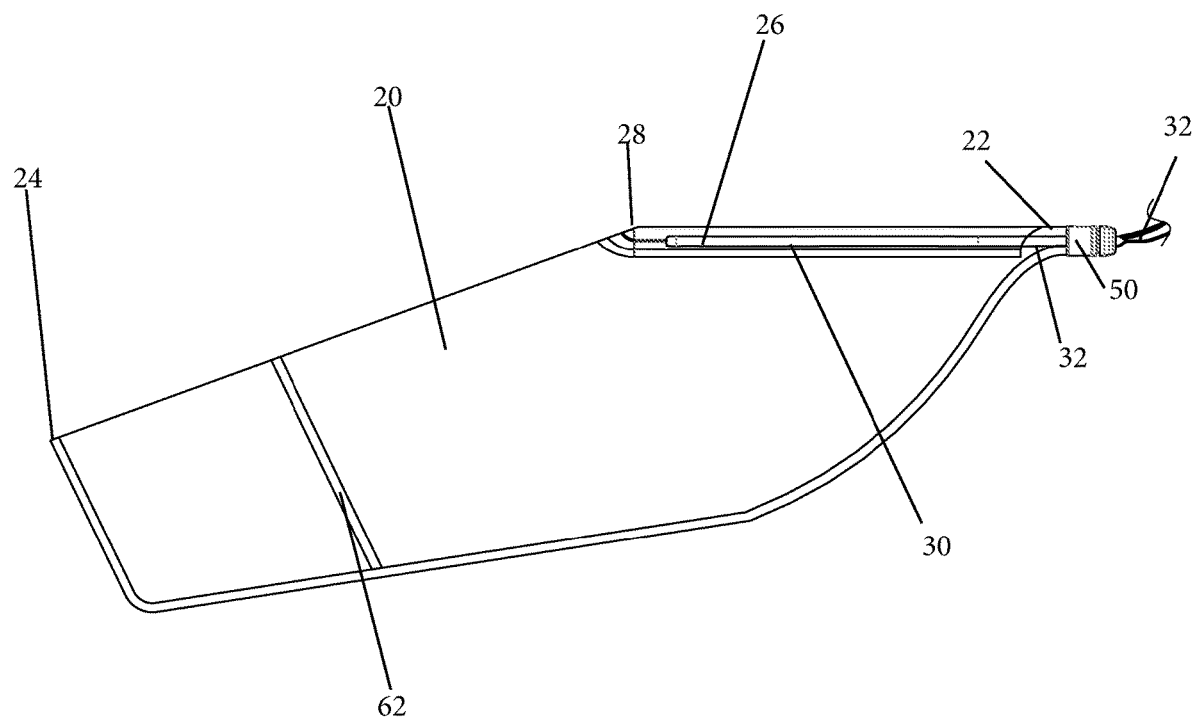
FIG. 4 is a side view of the tissue retrieval bag of the tissue retrieval system of FIG. 1.

With reference to FIGS. 2, 3, and 4, in some embodiments, the tissue retrieval system includes a retrieval bag 20 sized and configured to be contained within a relatively small (such as, for example, a 5-7 mm) diameter introducer tube while providing a retrieval bag with a similar size and volume as laparoscopic retrieval bags for use with 10 mm trocars. Advantageously, such a retrieval bag 20 can facilitate various laparoscopic surgical procedures with the use of relatively small single incision site surgical access points.

With continued reference to FIGS. 2, 3, and 4, in the illustrated embodiment, the tissue retrieval bag 20 has a distal end 24 opposite a proximal end 22. The illustrated tissue retrieval bag 20 includes a rim 26 defining an opening adjacent the proximal end 22 into the tissue retrieval bag 20, while the distal end 24 of the tissue retrieval bag 20 is closed. The material of the tissue retrieval bag 20 can be folded and sealed at the rim 26 to form a cuff 30. The cuff 30 can be sized and configured to receive the support arms and a cord loop 32. In certain embodiments, the cuff 30 can be non-continuous. In the illustrated embodiment, the tissue retrieval bag 20 has an elongate profile, with a portion of the tissue retrieval bag 20 extending distally from the rim 26 and the opening. The distally extending portion of the retrieval bag diverges at an angle transverse to the rim 26 of the bag 20.

Advantageously, this elongate profile allows the tissue retrieval bag 20 to have a relatively small outer diameter when in a stowed configuration (FIG. 1), while having a relatively large volume in a deployed configuration (FIGS. 2, 3, and 4). Thus, the tissue retrieval bag 20, in the stowed configuration, can fit within a relatively small diameter introducer tube 3. With reference to FIG. 4, in order to position the tissue retrieval bag 20 in the stowed configuration, the tissue retrieval bag 20 can be rolled about an axis generally parallel to a longitudinal axis defined by the rim 26 and the opening of the bag. Thus, in the stowed configuration, the distal end 24, and the distal-extending portion of the tissue retrieval bag 20 is positioned longitudinally distally of the rim 26 and the opening with respect to the axis defined by the rim 26. The tissue retrieval bag 20 in the stowed configuration can be stored within the introducer tube 3. The cross-sectional area at any point along the length of the rolled retrieval bag with respect to the longitudinal axis defined by the rim 26 is equivalent to or smaller than the cross-sectional area of a relatively small introducer tube, such as a 5-7 mm introducer tube. Likewise, the cross-sectional area at any point along the axis of the rolled retrieval bag 20 is decreased as compared to prior retrieval bags of approximately the same volume.

In one embodiment, the tissue retrieval bag 20 is sized such that the volume of the retrieval bag is approximately 180 mL and the tissue retrieval bag 20 in the stowed configuration fits within a 5-7 mm trocar introducer. In some embodiments, the volume of the tissue retrieval bag is greater than approximately 100 mL. Accordingly, a ratio of the volume of the retrieval bag to its stowed diameter can be relatively high, in the exemplary embodiment, approximately 26-36 mL/mm. In other embodiments, the tissue retrieval bag 20 can be sized such that the volume is between about 50 mL and 400 mL, desirably between about 100 mL and 350 mL, and more desirably between about 150 mL and 200 mL. In some embodiments, the volume of the retrieval bag 20 fit within a predetermined size trocar can be increased by further elongating the bag to enable a greater amount of tissue to be placed within the bag. For example, some embodiments of tissue retrieval bag for placement within a 5-7 mm trocar introducer can have a first length between the proximal end 22 and the distal end 24 and a first volume, while other embodiments of tissue retrieval bag for placement within a 5-7 mm trocar introducer can have a second length between the proximal end 22 and the distal end 24 and a second volume, where the first length is smaller than the second length and the first volume is smaller than the second volume.

In one embodiment, the retrieval bag 20 is configured from 4.2 mil (0.0042") thick polyurethane film. In some embodiments, the thickness of the polyurethane film can be greater than or less than 4.2 mil, such as, for example for use in extracting tissue of a relatively high or low weight. In some embodiments, the retrieval bag can be formed from a variety of materials including polyurethane, polyethylene, polyimide, ripstop Nylon®, polyester, and Mylar®. In some embodiments, the retrieval bag can be formed from laminated materials such as polyurethane coated ripstop Nylon, silicone coated ripstop Nylon, polyurethane coated ripstop polyester, silicone coated ripstop polyester, polyurethane coated taffeta, and polyurethane coated spandex. The thicknesses of any of these materials can be chosen based, at least partially, on considerations of tissue weight to be carried by the tissue retrieval bag and outer diameter of the tissue retrieval bag in a stowed configuration.

With reference to FIG. 4, in some embodiments, the bead 50 can include an expandable, relatively large diameter member such as a snap ring positioned about a periphery thereof. In the illustrated embodiment, an annular groove 52 extends around an outer surface of the guide bead to receive a snap ring. When positioned in the annular groove 52, the snap ring can prevent reentry of the guide bead 50 into the introducer 3 once the actuator 7 has advanced the retrieval bag 20 and guide bead 50 out of the introducer, thus facilitating cinching of the retrieval bag 20 when the cord 32 is pulled. In other embodiments a portion of bag material adjacent the guide bead 50 can facilitate cinching of the retrieval bag 20. For example, in these embodiments, the guide bead 50 can be pulled within the introducer 3 tube while the tissue retrieval bag 20 can collect and bunch up outside the introducer 3 tube when the cord is pulled.

During clinical use of a tissue retrieval system such as described above and illustrated in FIGS. 1-3, an access device such as a trocar is first placed through a body wall leaving the trocar cannula disposed across the body wall. The tissue retrieval system is then inserted into the trocar seal and cannula until the distal end of the introducer tube extends beyond the distal end of the trocar cannula. The retrieval bag is then deployed from within the introducer tube and into the body cavity by advancing the actuator in a distal direction. In certain embodiments, the actuator includes a ratcheting mechanism which allows distal movement of the actuator during retrieval bag deployment and prevents the actuator from being pulled in a proximal direction to ensure proper operation of the device. Once extended into the body cavity, the retrieval bag is suspended and held open by two support arms that extend into the cuff on the retrieval bag, as illustrated in the embodiment of FIGS. 2-3.

After a tissue retrieval bag has been deployed from the introducer, it is desirable to maintain the position of the tissue retrieval bag and guide bead relative to the support arms to restrict the guide bead from inadvertently being advanced along the support arms leaving a portion of the rim unsupported. It can be desirable to maintain the position of the tissue retrieval bag and guide bead during manual unfurling of the tissue bag and during insertion and manipulation of tissue specimens. Manual unfurling of the tissue bag is sometimes necessary during use of the device to enable the insertion of tissue specimens. Manual unfurling is typically achieved by inserting a blunt grasper or other blunt instrument into the opening of the retrieval bag and applying a downward force to unroll or unfurl the retrieval bag. In some cases, during manual unfurling of the retrieval bag, an axial force along the longitudinal axis of the device can be applied to the retrieval bag causing unintentional movement of the retrieval bag along the support arms. During insertion of tissue specimens into the retrieval bag and during manipulation of inserted tissue specimens, an axial force can also be applied to the retrieval bag causing unintentional movement of the retrieval bag along the support arms.

Inadvertent movement of the retrieval bag relative to the support arms can result in the partial closure of the opening of the retrieval bag as it slides along the support arms which can make it difficult to subsequently insert tissue specimens into the opening. As the retrieval bag with the attached bead slides along the support arms, the slots on the bead, through which the supports are positioned, advance into the radiused sections of the support arms causing the support arms to toe inward reducing the size of the retrieval bag opening. In some cases, the retrieval bag can slide completely off of the support arms. In various embodiments, the tissue retrieval systems described herein further comprise retention features for restricting inadvertent movement of the retrieval bag relative to the support arms.

With the tissue retrieval bag maintained in a deployed, open configuration throughout manual unfurling and manipulation within the surgical site, tissue specimens can be placed in the tissue retrieval bag during a surgical procedure. The tissue retrieval systems described herein can be configured to facilitate closing of the tissue retrieval bag when desired by a user. The retrieval bag can include an integral bead through which the support arms slide. The retrieval bag also includes a cord loop which runs through the cuff of the retrieval bag and is releasably attached to the actuator. As further described herein with respect to the illustrated embodiments, the bead can include a passage through which the cord loop runs that frictionally engages the cord loop to enable the retrieval bag to be cinched closed and reopened as desired. Once a tissue specimen such as a gallbladder is separated from the adjoining vessels and structures, it can then be placed into the retrieval bag. The actuator is then pulled proximally to withdraw the support arms from the cuff and the bead on the retrieval bag. The actuator includes a ratcheting mechanism which allows proximal movement of the actuator during cinching of the retrieval bag and prevents distal movement of the actuator to ensure proper and complete closure of the retrieval bag. As the support arms are pulled out of the cuff of the retrieval bag and through the bead, tension is then applied to the cord loop to cinch the bag closed. Once the retrieval bag is fully closed, a small loop of the cord is exposed on the actuator near the proximal end of the introducer tube.

The cord loop can desirably be dimensioned such that its length enables cinching of the retrieval bag and exposure of the cord loop on the actuator after cinching. When the retrieval bag is cinched closed, the cord loop is fully tensioned. In certain of the illustrated embodiments of tissue retrieval system, the cord loop is initially fully contained within the introducer tube of the retrieval system such that it is inaccessible to the surgeon and is only exposed to the surgeon upon cinching of the retrieval bag. This inaccessible positioning prevents the surgeon from unintentionally grasping, cutting, releasing, or tensioning the cord loop prior to deployment of the retrieval bag. The cord loop is stored in the introducer tube in a non-tensioned condition with a portion of the cord loop being folded and stored in a receiving channel on the underside of the actuator.

There are at least two methods for withdrawal of the retrieval bag from within the body cavity. For the first method, the retrieval bag can be completely detached and removed from the actuator and introducer tube by lifting the cord loop from the retaining slot on the actuator. The device and the trocar seal and cannula can then be withdrawn from the body wall leaving the retrieval bag in the body cavity and the cord loop disposed across the body wall. The neck of the retrieval bag can then be withdrawn through the body wall using the bead as a dilator to aid with movement of the retrieval bag through the layers of tissue fibers in the body wall. Once the neck of the retrieval bag has traversed the body wall, the retrieval bag can then be reopened by manually grasping the closed end of the retrieval bag and the bead and sliding the bead along the cord. The retrieval bag can then be accessed to remove or compact its contents to aid with complete withdrawal from the body cavity using standard open and endoscopic instrumentation such as forceps, graspers, and aspiration probes. Once the bulk of the contents are removed, the retrieval bag can then be closed by manually grasping the cord loop and the bead and sliding the bead along the cord. The cord loop can then be manually tensioned to completely withdraw the tissue retrieval bag from the body cavity.

The second method for withdrawal of the retrieval bag from within the body cavity can be used for small tissue specimens placed in the retrieval bag which are not likely to need to be aspirated, compacted, or removed from the retrieval bag prior to withdrawal of the retrieval bag through the body wall. In this case, the cord loop can be left attached to the actuator and the entire device along with the trocar seal and cannula can be simultaneously withdrawn from the body cavity and through the body wall.

Figure 5:
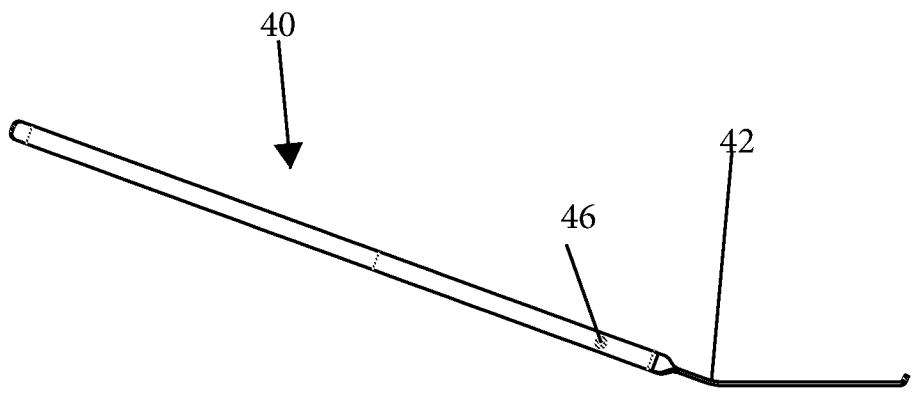
FIG. 5 is a side view of one support arm of the tissue retrieval system of FIG. 1.
Figure 6:
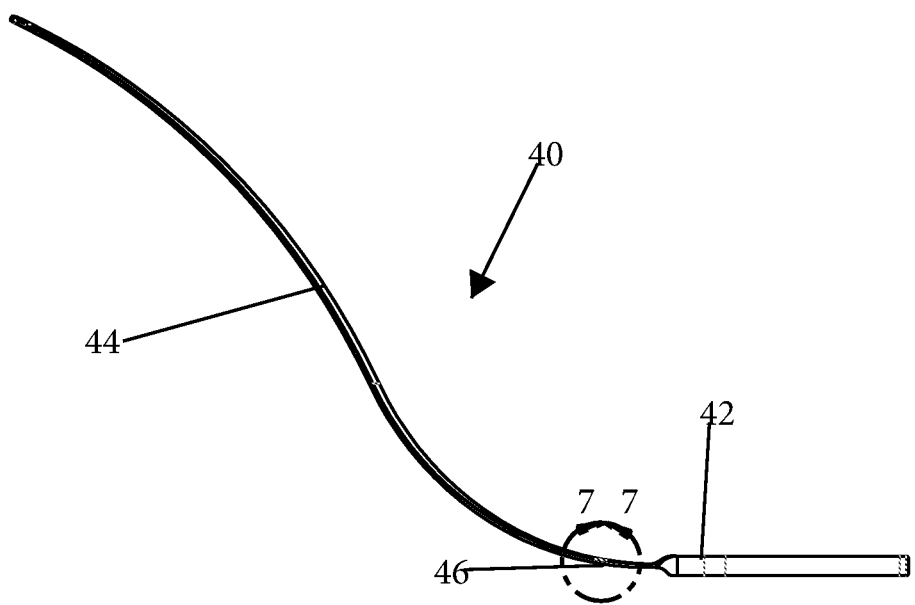
FIG. 6 is a top view of the support arm of FIG. 5.

With reference to FIGS. 2, 5, and 6, in some embodiments, the tissue retrieval systems 10 described herein include retrieval bag support arms 40 which are biased to a predetermined position when the tissue retrieval system is in the deployed configuration. For example, in the illustrated embodiment, the support arms 40 are biased to spring radially outward and transversely upward with respect to a longitudinal axis defined by the introducer 3 upon deployment of the retrieval bag 20 from the introducer 3. Desirably, by springing transversely upward upon deployment of the retrieval bag 20, the support arms create an access position having an angled entry for the rim 26 of the retrieval bag 20 relative to the axis of the introducer 3. Advantageously, the angled entry facilitates the loading of tissue specimens during laparoscopic procedures as it allows a grasped tissue sample to be easily disposed within the retrieval bag 20. This ease of loading can be particularly advantageous for single incision laparoscopic procedures where the grasped tissue is held by a grasper that is disposed through the same incision as the retrieval system introducer 3. Thus, the transverse orientation of the retrieval bag 20 rim 26 relative to the longitudinal axis of the introducer 3 enables a tissue specimen held by a grasper to be easily inserted and pushed towards the distal end 24 of the retrieval bag 20 during single incision laparoscopic procedures where it would otherwise be particularly difficult to create a substantial axial angle between the grasper shaft and the introducer tube.

With continued reference to FIGS. 2, 5, and 6, in some embodiments, a tissue retrieval system can include support arms 40 designed to flex open and upward upon deployment of the retrieval bag 20 from within the introducer 3 tube to facilitate the loading of a tissue specimen sample during standard laparoscopic procedures and during single incision laparoscopic procedures. As illustrated, the support arms 40 can be bent to include upward bends 42 in each support arm 40 in the sections of the support arms that are proximal to where a bead 50 is positioned and distal to the end of the actuation rod. When viewed from a top perspective, as illustrated in FIG. 6, each of the support arms 40 can also include a radial bend, curve, or curved profile 44. As the retrieval bag 20 is advanced out of the introducer 3, the support arms 40 spring radially outward to return to the radial curved profile 44, thus opening the retrieval bag. As the retrieval bag 20 is further advanced out of the introducer 3, the support arms 40 spring upward about the bends 42 in the support arms 40 to position the retrieval bag 20 in the access position with an angled opening relative to the longitudinal axis of the introducer 3. As the retrieval bag 20 is cinched closed, the support arms 40 flex downward and radially inward as they are retracted into the introducer 3.

In some embodiments, the support arms 40 can be formed from 17-7PH stainless steel, which is a typical spring metal. In other embodiments, the support arms 40 can comprise other metals and metal alloys having desired biasing properties. In other embodiments, the support arms 40 can be formed of a memory metal such as a nickel titanium alloy or nitinol metal. The memory metal can be preshaped to be generally linear in the introducer 3 with the tissue retrieval system in the initial configuration and to form a radially expanded and transversely bent shape upon application of body heat to the support arm 40 as the tissue retrieval bag 20 is deployed into a body cavity.

Instead of, or in addition to the biased support arms 40 discussed above, in some embodiments, the support arms can pivot about a pin and the tissue retrieval system can include a torsion spring to drive the support arms upward upon deployment from the introducer tube. This spring-biased pivot mechanism can provide the retrieval bag with an angled opening relative to the longitudinal axis of the introducer tube.

Figure 7:
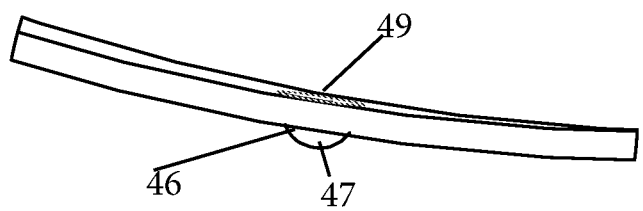
FIG. 7 is a detail view of the support arm of FIG. 6.

With reference to FIGS. 5-7, the illustrated support arms 40 include one embodiment of retention feature to maintain a position of the tissue retrieval bag relative to the support arms during unfurling, tissue insertion, and manipulation of tissue specimens. In the illustrated embodiment, the retention feature comprises a raised dome 46 or dimple formed on the support arms 40. The dome 46 can be applied to a support arm 40 through a punch or embossing technique such that the support arm comprises a raised dome surface 47 on a first side of the support arm 40 and a corresponding recess 49 on a second side of the support arm opposite the first side.

With continued reference to FIGS. 5-7, the dome 46 can be positioned on the support arm 40 at a location corresponding to a position to retain the guide bead 50 with the tissue retrieval bag 20 in a deployed and open configuration. (FIGS. 2, 3). In the illustrated embodiment, the dome 46 is positioned distal of the bends 42 and at a proximal region of the curved profile 44. In other embodiments, a dome can be positioned at another location on the support.

With reference to FIGS. 8-9, an embodiment of guide bead 50 that can be used in the tissue retrieval systems described herein is illustrated. As illustrated, the guide bead comprises a generally cylindrical profile having an outer diameter sized to fit within a lumen of the introducer of the tissue retrieval system. The guide bead 50 can include a proximal end 51 having a radiused or tapered profile that can facilitate tissue dilation as the tissue retrieval bag is withdrawn from a surgical site through an incision.

With continued reference to FIGS. 8-9, the guide bead 50 can include at least one slot 54 extending generally longitudinally therethrough to receive a support arm of the tissue retrieval system. As illustrated, the guide bead 50 includes two laterally offset generally parallel slots 54 to receive a pair of support arms for the tissue retrieval system. The guide bead 50 can further comprise an aperture 56 that opens to a passage 58. The aperture 56 and passage 58 can be sized and configured to slidably receive a cord and frictionally engage the cord such that the guide bead can be slid along the cord to open and close the tissue retrieval bag and to maintain the tissue retrieval bag in a cinched or partially cinched configuration.

With reference to FIGS. 10-12, the guide bead 50 is illustrated in an initial position on a pair of support arms 40 for a tissue retrieval system such as that described and illustrated in FIGS. 1-3. In the illustrated embodiment, the guide bead comprises two-piece assembly having a first, proximal portion 62 and a second, distal portion 64 snap fit thereto. In certain embodiments, a portion of the tissue retrieval bag can be positioned between and engaged by the assembly of the first portion 62 and the second portion 64. In the initial position, corresponding to the stowed and deployed and open configurations of the tissue retrieval bag from the introducer of the tissue retrieval system, the guide bead 50 is positioned on the support arms 40 such that the support arms extend through the slots 54 of the guide bead 50 with the domes 46 positioned distal of the slots 54.

With continued reference to FIGS. 10-12, the dimples or domes 46 can be desirably dimensioned such that the dimpled section of each support arm 40 has a width W1 that is greater than the width W2 of the corresponding slot 54 in the bead 50. For example, in one embodiment, the width W1 of the dimpled section of each support arm 40 in an exemplary tissue retrieval system configured for insertion through a 5 mm access port is about 0.024" while the width of each corresponding slot 54 on the guide bead 50 is approximately 0.021". In other embodiments of tissue retrieval systems sized and configured for insertion through different sized access ports such as 10 mm, 12 mm, or 15 mm instrument size category trocars, it can be desirable that the difference between the width W1 of the dimpled section of support arm and the width W2 of the slots 54 of the bead 50 are at least approximately 0.003". In certain embodiments, the bead 50 is formed of polycarbonate polymer and the slots 54 deform slightly as they interface with the dimples on the support arms 40.

With reference to FIGS. 11-12, an initial movement of the guide bead with respect to the support arms 40 is illustrated. FIG. 11 illustrates the bead 50 and support arm 40 assembly with the guide bead 50 in a fully proximal position, corresponding to the stowed and initially deployed configurations of the tissue retrieval bag. FIG. 12 illustrates the bead 50 and support arm 40 assembly as the bead 50 is initially advanced distally relative to the support arms 40. This distal movement can be intentional, such as by a user beginning to retract the actuator to cinch the tissue retrieval bag and withdraw the support arms from the tissue retrieval bag. Or, the movement can be inadvertent, due to manipulation of the tissue retrieval system and forces applied to the bag or actuator by a user, the anatomy of a surgical site, or another instrument in the surgical site. As illustrated in FIG. 12, the dimples or domes 46 are sized and configured to provide resistance to inadvertent movement of the bead, but allow the support arms to be pulled through the slots in the bead at a given force during cinching of the retrieval bag. For example, in some embodiments, the resistance provided by the dimpled sections of the support arms 40 may be approximately 4 lbs. of axial force, which is sufficient to prevent inadvertent movement of the retrieval bag along the supports but low enough to enable cinching of the retrieval bag by the surgeon at an acceptable axial force during retraction of the actuator.

While it can be desirable that approximately 4 lbs. of axial force is required to advance the bead 50 over the domed section of the support arms 40, in other embodiments, more or less than 4 lbs of axial force can advance the domes 46 longitudinally through the slots 54 of the bead 50. The axial force required for movement of the guide bead 50 can be increased or decreased from the illustrated embodiment by varying certain aspects of one or both of the guide bead and support arms. For example, in certain embodiments, a width W2 of the slot 54 of the guide bead 50 or a width W1 of the dome 46 can be different from the embodiment discussed above to raise or lower the axial force required to slide the guide bead 50 over the dimpled portion of the support arms 40. Moreover, in certain embodiments, the guide bead 50 can be formed of a material other than a polycarbonate polymer material such that more or less axial force is required to advance the guide bead 50 over the dimpled portion of the support arms 40. In other embodiments, only one of the pair of support arms has a domed or dimpled portion, while the other support arm has no retention feature. In still other embodiments, the positioning of the dimples on the support arms can be axially staggered rather than axially aligned to provide a first resistance and a secondary resistance to prevent inadvertent movement of the bead and retrieval bag relative to the support arms. If the first resistance from the dimple on the first support arm is overcome, the secondary resistance provided by the dimple on the second support arm can prevent additional inadvertent movement of the bead and retrieval bag.

In still other embodiments, other arrangements of domes or dimples can be selected to achieve a desired axial force for movement of the bead 50 relative to the support arms 40. For example, in some embodiments, each support arm can include two or more dimples to provide primary and secondary resistances to inadvertent movement of the bead and retrieval bag. In the illustrated embodiment, the domes protrude radially inwardly with respect to the lumen of the introducer with the tissue retrieval bag stowed in the introducer. In other embodiments, the dimples or domes can be positioned to protrude radially outwardly. In one embodiment, a support arm includes multiple dimples on each support, and the dimples can be positioned on both sides of the support arms.

While the support arm and guide bead assembly illustrated in FIGS. 10-12 includes domed or dimpled support arms which are axially restrained by slots in the guide bead, it is contemplated that in other embodiments, similar retention forces can be generated by other configurations of a support arm or guide bead. For example, in certain embodiments, it is contemplated that rather than punched or embossed dimple features formed on the support arms, the support arms can include a retention segment having welded or bonded material that locally increases thickness of the support arms and provides resistance to inadvertent movement of the bead but allows the support arms to be pulled through the slots in the bead at a given force. In certain embodiments, the material can comprise one or more of a metal, polymer, polymer film, or elastomer material. In other embodiments, the guide bead can include an elastomeric insert fitted, bonded, or over-molded into the distal end of the bead. The insert would include slots for the support arms sized to frictionally engage the support arms to provide resistance to inadvertent movement of the bead but allow the support arms to be pulled through the slots in the insert at a given force during cinching of the retrieval bag.

With reference to FIGS. 13-21, in certain embodiments of tissue retrieval systems, a distal end cap of the actuator can be configured to releasably engage the guide bead. This releasable engagement maintains a position of the guide bead with respect to the actuator to reduce the potential for inadvertent movement of the guide bead along the support arms. However, when a user desires to cinch the tissue retrieval bag and remove the support arms from the cuff of the bag, application of an axial withdrawal force to the actuator disengages the actuator cap from the guide bead to allow the tissue retrieval bag to be cinched closed.

With reference to FIGS. 13-16, an embodiment of guide bead 100 and actuator cap 107 having a releasably engageable connection is illustrated. The guide bead 100 is substantially similar to the guide bead 50 described with reference to FIGS. 8-9. The guide bead 100 can comprise a pair of slots 104 sized and configured to receive support arms therethrough and an aperture 106 for receiving a cord therethrough. In contrast to the guide bead 50 illustrated in FIGS. 8-9, guide bead 100 further comprises an engagement feature such as a recess or ledge 110 formed therein. As illustrated, the ledge 110 is formed adjacent a proximal end of the bead 100.

With continued reference to FIGS. 13-16, the actuator cap 107 can comprise a protrusion such as a cantilever hook 117 extending therefrom. The cantilever hook 117 can extend generally longitudinally distally from a distal end of the actuator cap 107 and a mating hook 119 can be positioned at the distal end of the cantilever hook 117. With the bead 100 abutting the actuator cap 107, such as with a tissue retrieval system having a tissue retrieval bag in a stowed or initial deployed, open configuration as illustrated in FIGS. 1-3, the cantilever hook 117 is positioned adjacent the ledge 110 of the bead 100. The mating hook 119 at the distal end of the cantilever hook 117 is configured to releasably latch with the ledge 110 on the bead. The mating hook 119 includes an angled contact surface that engages with the ledge on the bead. The angled contact surface 121 causes the hook to deflect upwards during cinching of the bag to allow the ledge 110 of the bead 100 to disengage from the cantilever hook 117. Thus, the cantilever hook 117 can desirably prevent unintentional sliding of the bead and retrieval bag relative to the support arms. The releasable engagement of the cantilever hook 117 and bead 100 provides resistance to inadvertent movement of the bead 100, but allows the bead 100 to slide relative to the support arms at a given force during cinching of the retrieval bag.

Figure 17:
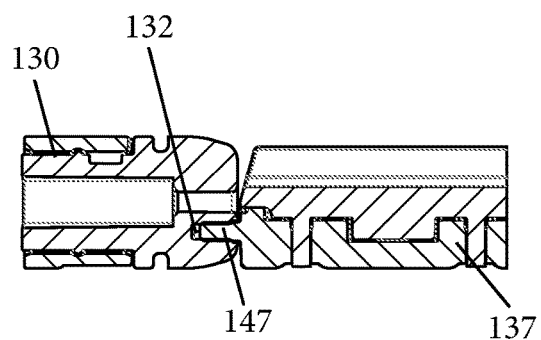
FIG. 17 is a cross-sectional side view of another embodiment of guide bead and actuator cap.
Figure 18:
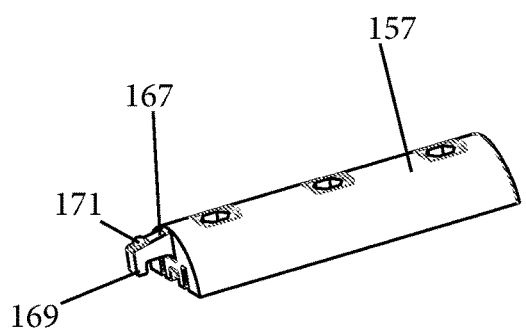
FIG. 18 is a perspective view of another embodiment of actuator cap for use with an embodiment of guide bead.
Figure 19:
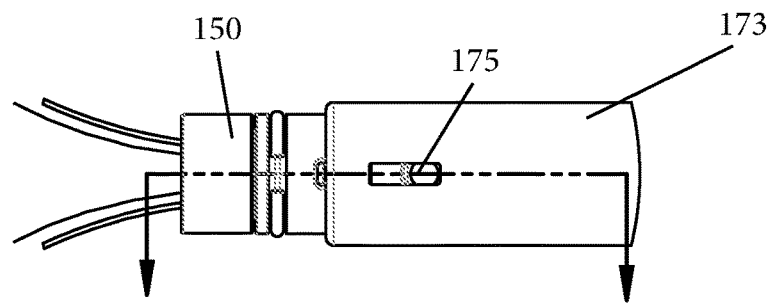
FIG. 19 is a bottom view of the actuator cap of FIG. 18 and a guide bead positioned in an embodiment of introducer tube of a tissue retrieval system.

With reference to FIG. 17, another embodiment of guide bead 130 and actuator cap 127 having a releasably engageable connection is illustrated. The guide bead 130 is substantially similar to the guide bead 100 described with reference to FIG. 13. However, rather than the ledge 110 of the guide bead 100 of FIG. 13, guide bead 130 comprises a bore or hole 132 formed at the proximal end thereof. The actuator cap 137 can include a protrusion such as a pin 147 or a series of pins that extend from the distal end of the actuator cap 137 into the proximal end of the bead. With the actuator cap 137 abutting the bead 130, the pin 147 is positioned in the hole 132 of the bead. With this engagement, the pin 147 presses into and lightly interferes with the hole 147 to releasably attach the bead and retrieval bag to the actuator. The attachment of the bead to the actuator provides resistance to inadvertent movement of the bead and the retrieval bag, but allows the bead to release from the actuator at a given force allowing the bead to slide relative to the support arms during cinching of the retrieval bag. While the section view of FIG. 17 illustrates a single pin 147 extending from the actuator cap 137 and a corresponding single hole 132 formed in the bead 130, it is contemplated that in other embodiments, the actuator cap 137 can comprise two or more pins 147 protruding therefrom and the bead can comprise a corresponding two or more holes 132 formed therein. In various embodiments, the holes 132 for the pins 147 can be circular, hexagonal, or another geometric shape.

With reference to FIGS. 18-21, an embodiment of guide bead 150 and actuator cap 157 having a releasably engageable connection is illustrated. The guide bead 150 is substantially similar to the guide bead 100 described with reference to FIG. 13. The guide bead 150 can comprise an engagement feature such as a recess or ledge 160 formed therein. As illustrated, the ledge 160 is formed adjacent a proximal end of the bead 150.

Figure 20:
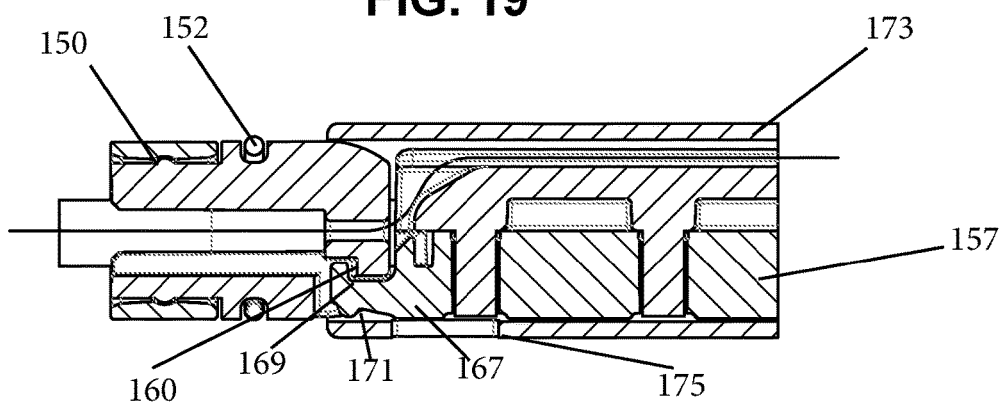
FIG. 20 is a cross sectional side view of the actuator cap and guide bead of FIG. 19 in a coupled configuration.

With continued reference to FIGS. 18-21, the actuator cap 157 can comprise a protrusion such as a cantilever hook 167 extending therefrom. The cantilever hook 167 can extend generally longitudinally distally from a distal end of the actuator cap 157 and a mating hook 169 can be positioned at the distal end of the cantilever hook 167. With the bead 150 abutting the actuator cap 157, such as with a tissue retrieval system having a tissue retrieval bag in a stowed or initial deployed, open configuration as illustrated in FIGS. 1-3, the cantilever hook 167 is positioned adjacent the ledge 160 of the bead 150. As illustrated in FIG. 20, the mating hook 169 at the distal end of the cantilever hook 167 is configured to releasably latch with the ledge 160 on the bead.

Figure 21:
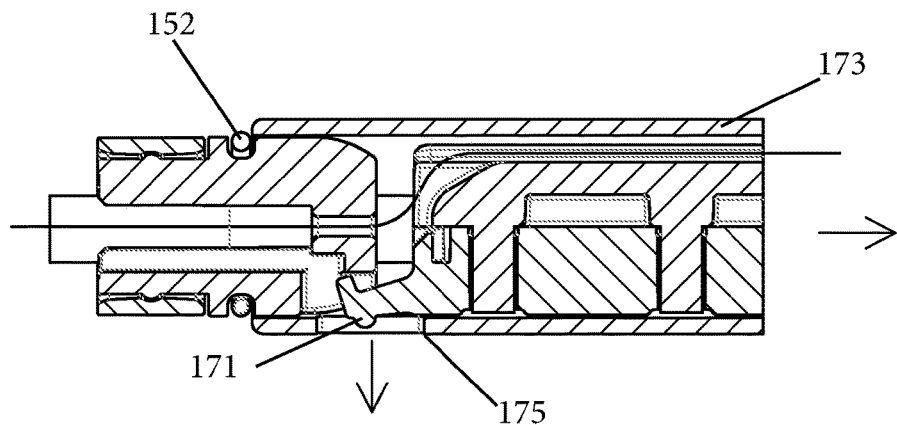
FIG. 21 is a cross sectional side view of the actuator cap and guide bead of FIG. 19 in a decoupled configuration.

With continued reference to FIGS. 18-21, the cantilever hook 167 can be sized and configured such that it cannot deflect a sufficient distance within the introducer tube 173 to allow release of the ledge 160 of the bead 150 until adequate clearance is provided for the cantilever hook 167 to deflect. The clearance can be provided by a mating slot or hole near the distal end of the introducer tube 173. The cantilever hook 167 would only deflect a sufficient distance to allow release of the bead 150 when the actuator is retracted during cinching of the retrieval bag. In the illustrated embodiment, the cantilever hook 167 includes a latch protrusion 171 that extends radially outwardly and can engage with an inner surface of the lumen of the introducer tube 173. The introducer tube 173 is similar to the introducer 3 described above with reference to FIGS. 1-3. The introducer tube 173 can further comprise a hole or slot 175 positioned adjacent the distal end. This slot 175 can provide clearance for the latch protrusion 171 when the actuator and actuator cap are retracted to a predetermined position (FIG. 21). With the actuator and actuation cap retracted to the predetermined position, a snap ring 152 interferes with the distal end of the introducer tube and prevents the guide bead 150 from further reentering the introducer tube 173. When the actuator has been retracted to position the latch protrusion 171 in the slot 175 of the introducer tube 173, the cantilever hook 167 deflects radially outward and allows the mating hook 169 to disengage from the ledge 160 of the bead 150. Thus, the cantilever hook 167 can desirably prevent unintentional sliding of the bead and retrieval bag relative to the support arms with the tissue retrieval bag positioned in an initial deployed and open configuration. The releasable engagement of the cantilever hook 167 and ledge 160 provides resistance to inadvertent movement of the bead 150, but allows the bead 150 to slide relative to the support arms at a given force during cinching of the retrieval bag.

While FIGS. 13-21, illustrate certain releasable mechanical engagements between an actuator cap and guide bead of a tissue retrieval system, in other embodiments, a guide bead can be releasably welded or bonded to the actuator cap and/or the actuator to provide resistance to inadvertent movement of the bead and the retrieval bag, but allow the bead to release from the actuator cap and/or actuator at a given force allowing the bead to slide relative to the support arms during cinching of the retrieval bag. For example, in various embodiments the bead can be ultrasonically welded, thermally welded, or adhesively bonded to the actuator cap and/or actuator with a weld or bond strength selected to separate upon application of a predetermined tensile force to the actuator.

With reference to FIGS. 22-53, in certain embodiments of a tissue retrieval system, retention of the tissue retrieval bag relative to the support arms can be provided by various retention features that frictionally engage the cord loop. This frictional engagement can restrict movement of the cord loop. The tissue retrieval system can be assembled with a section of the cord loop distal this frictional engagement having a relatively small amount of slack, a light tension, or a length that generates neither slack nor tension. With the cord loop frictionally engaged, a small amount of movement of the retrieval bag and guide bead can be accommodated (until any slack in the cord loop is removed), but a force applied to the retrieval bag or guide bead would create tension in the cord loop distal of the frictional engagement. This cord loop tension resists inadvertent movement of the tissue retrieval bag and guide bead relative to the actuator and support arms of the tissue retrieval system.

Figure 22:
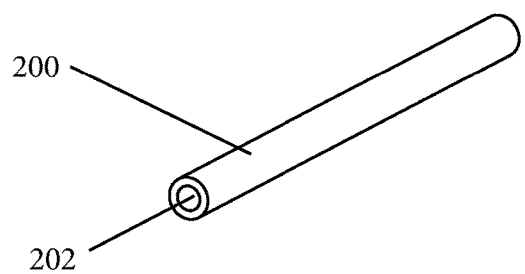
FIG. 22 is a perspective view of an embodiment of cord retention tube of a tissue retrieval system.
Figure 23:
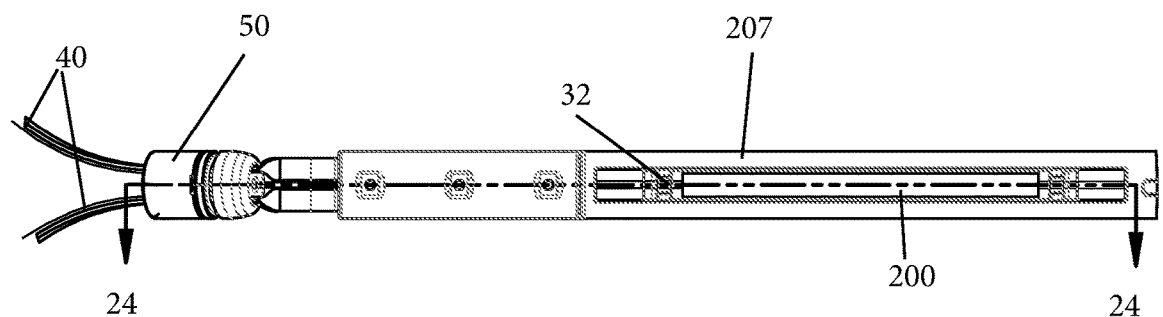
FIG. 23 is a bottom view of a distal end of an embodiment of tissue retrieval system having the cord retention tube of FIG. 22.
Figure 24:
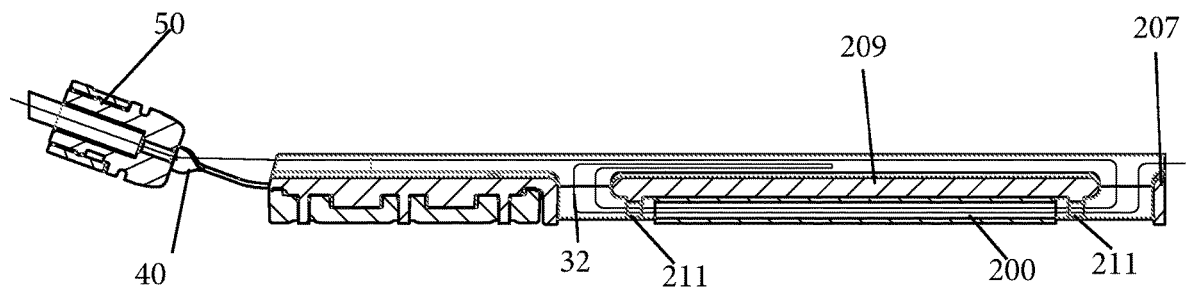
FIG. 24 is a cross sectional side view of the tissue retrieval system of FIG. 23.

With reference to FIGS. 22-24, in certain embodiments, a tissue retrieval system can include a cord retention tube or drag tube 200 to frictionally engage a portion of the cord loop 32. As illustrated in FIG. 22, the drag tube 200 can comprise a tubular member formed from a polymer material such as polyethylene or an elastomeric material such as silicone. The cord retention tube can define a lumen 202 extending therethrough. The lumen 202 has an inner diameter sized to frictionally engage the cord loop.

With continued reference to FIGS. 22-24, the actuator 207 of a tissue retrieval system can comprise a receiving channel 209 in which a portion of the cord loop 32 is stored. In the illustrated embodiment, the receiving channel 209 is configured to receive the cord retention tube 200 therein. The cord retention tube is held in place by the introducer tube. To prevent axial movement of the retention tube within the receiving channel 209, the actuator 207 can include a slotted wall 211 that acts as a stop for the retention tube, but allows the cord to be pulled through the slot. With the guide bead 50 positioned adjacent to the actuator 207 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 209 on the actuator 207 can be inserted into the cord retention tube or drag tube 200 and frictionally engaged by the lumen 202 of the drag tube 200.

In the illustrated embodiments, the cord retention tube prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 retrieval bag is provided while allowing the guide bead 50 and retrieval bag to slide relative to the support arms 40 at a given force during cinching of the retrieval bag. In certain embodiments, the cord loop 32 can be stored within the drag tube 200 with the ends of the cord extending completely through the tube. In other embodiments, the cord loop 32 can be stored within the drag tube 200 with the ends of the cord contained within the tube. During cinching of the retrieval bag, storage of the cord with its ends completely contained within the retention tube ensures a relatively constant frictional retention force while storage of the cord with its ends extending through the tube can result in a small increase in the frictional retention force as the ends of the cord are pulled into the retention tube.

Figure 25:
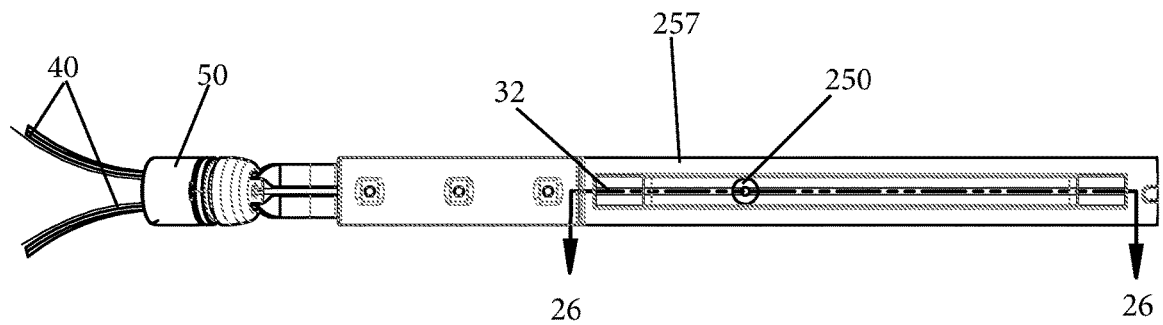
FIG. 25 is a bottom view of a distal end of an embodiment of tissue retrieval system having a cord retention o-ring.
Figure 26:
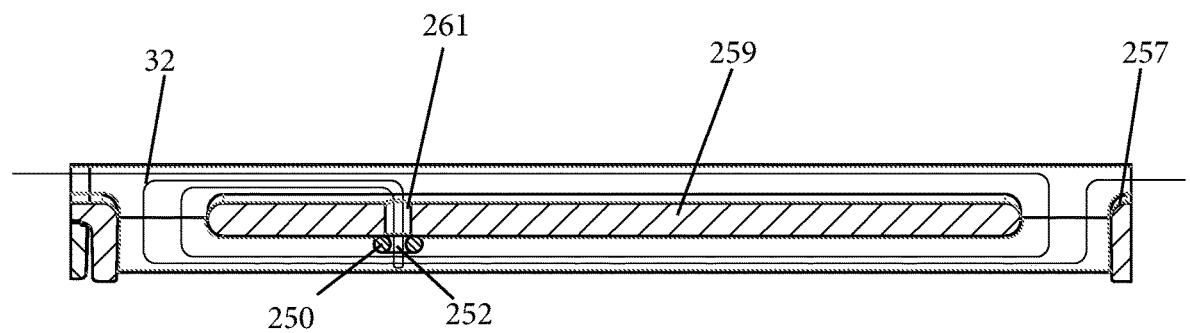
FIG. 26 is a cross sectional side view of the tissue retrieval system of FIG. 25.

With reference to FIGS. 25-26, in certain embodiments, a tissue retrieval system can include a retention ring such as an o-ring 250 to frictionally engage the cord loop 32. The o-ring 250 can be formed from various elastomeric materials such as silicone, ethylene propylene diene monomer (EPDM), polyurethane, and nitrile rubber. The o-ring can define an aperture 252 formed therein. The aperture 252 has an inner diameter sized to frictionally engage the cord loop.

With continued reference to FIGS. 25-26, the actuator 257 of a tissue retrieval system can comprise a receiving channel 259 in which a portion of the cord loop 32 is stored. In the illustrated embodiment, the receiving channel 259 is configured to receive the o-ring 250 therein. The receiving channel 259 can comprise a bore, cylinder or hole 261. The o-ring 250 can be positioned within the receiving channel such that the aperture 252 of the o-ring 250 is aligned with the hole 261. In certain embodiments, the o-ring 250 can be affixed to the receiving channel 259 such as by bonding in place with an adhesive. In other embodiments, the hole 261 can be sized with a cylindrical feature that receives the o-ring therein. With the guide bead 50 positioned adjacent to the actuator 207 such that the guide bead 50 is positioned at a proximal position on the support arms 40 (which corresponds to a stowed or initially deployed, tissue retrieval bag open configuration of a tissue retrieval system as illustrated in FIGS. 1-3), a portion of the cord loop 32 that is stored in the receiving channel 259 on the actuator 257 is inserted through the hole 261 and then through the aperture 252 of the o-ring 250. The inside diameter of the aperture 252 of the o-ring 250 frictionally engages the cord loop 32 and restricts unintentional movement of the retrieval bag by constraining the stored portion of the cord loop 32 and maintaining the remaining cord loop within the introducer tube in a tensioned condition.

With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag. When the retrieval bag is cinched closed, the stored portion of the cord loop 32 will pull through the o-ring 250 at a given force leaving the o-ring 250 trapped within the receiving channel 259 on the actuator 257.

Figure 27:
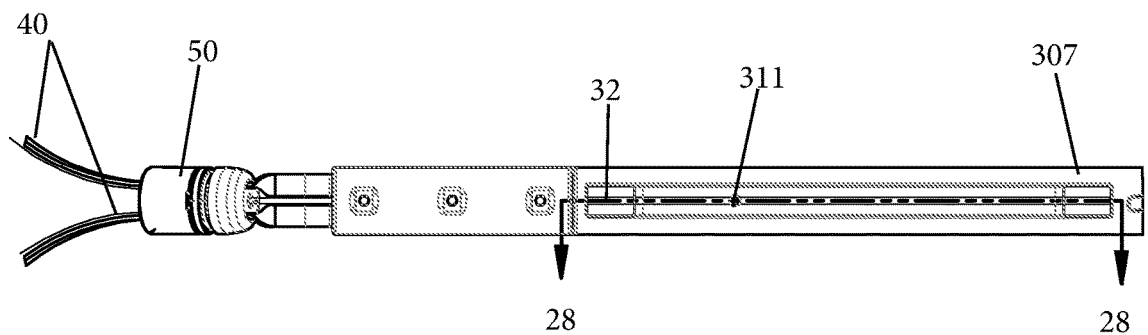
FIG. 27 is a bottom view of a distal end of an embodiment of tissue retrieval system having a cord engagement aperture.
Figure 28:
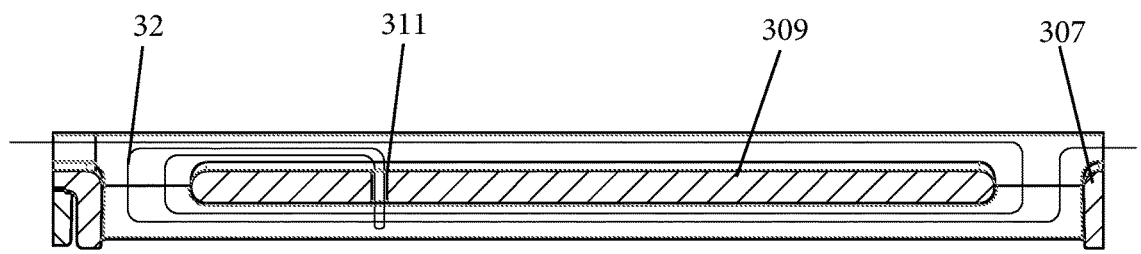
FIG. 28 is a cross sectional side view of the tissue retrieval system of FIG. 27.

With reference to FIGS. 27-28, in certain embodiments, a tissue retrieval system can include an actuator 307 having at least one retention port such as a bore or hole 311 to frictionally engage the cord loop 32. The hole 311 can have an inner diameter sized to frictionally engage the cord loop.

With continued reference to FIGS. 27-28, the actuator 307 of a tissue retrieval system can comprise a receiving channel 309 in which a portion of the cord loop 32 is stored. In the illustrated embodiment, the receiving channel 309 has a hole 311 formed therein. In certain embodiments, the receiving channel 309 can further comprise slotted or cored sections surrounding the hole 311 to allow for some flexibility as the ends of the cord loop 32 are pulled through the hole to minimize any increases in the frictional retention force during cinching of the retrieval bag. Alternatively, the ends of the cord loop 32 can be completely contained within the hole to ensure that the frictional force provided by the hole remains constant during cinching of the retrieval bag. With the guide bead 50 positioned adjacent to the actuator 307 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 309 on the actuator 307 is inserted through the hole 311. The inside diameter of the hole 311 frictionally engages the cord loop 32 and restricts unintentional movement of the retrieval bag by constraining the stored portion of the cord loop 32 and maintaining the remaining cord loop within the introducer tube in a tensioned condition.

With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag. When the retrieval bag is cinched closed with the given force, the stored portion of the cord loop 32 will pull through the hole 311.

While the illustrated embodiment includes a hole 311 formed in the receiving channel 309 of the actuator 307, in other embodiments, it is contemplated that a separate molded insert with a formed hole for frictionally engaging the cord loop can be inserted into the actuator. The separate insert can be molded from a lower durometer polymer such as polyethylene or polyurethane than that used for the actuator to minimize any increases in the frictional retention force during cinching of the retrieval bag.

Figure 29:
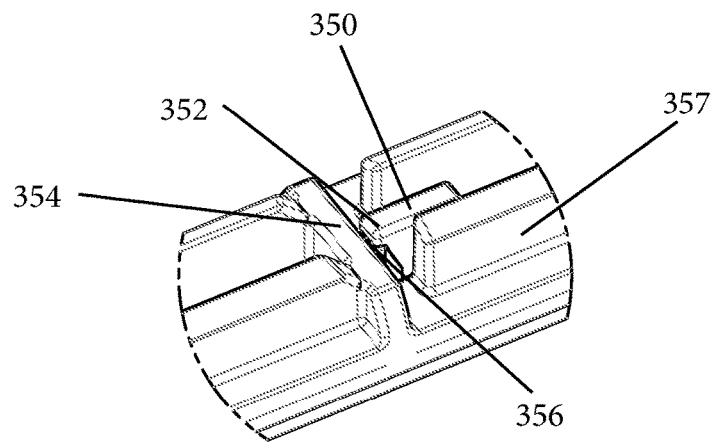
FIG. 29 is a perspective view of an actuator having a cord retention slot for an embodiment of tissue retrieval system.
Figure 30:
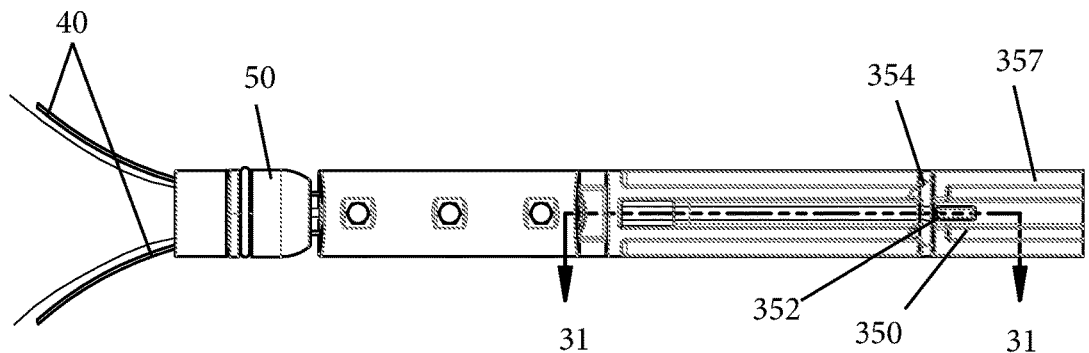
FIG. 30 is a bottom view of a distal end of an embodiment of tissue retrieval system having the actuator of FIG. 29.
Figure 31:
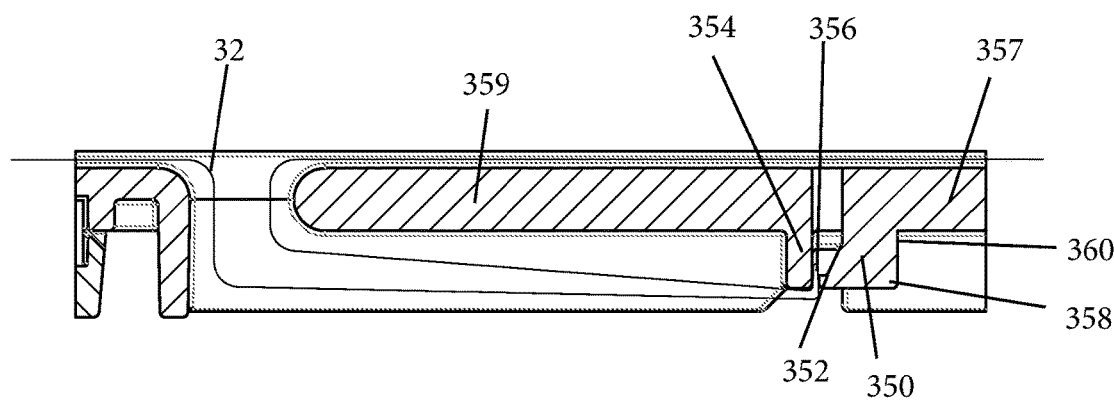
FIG. 31 is a cross sectional side view of the tissue retrieval system of FIG. 30.

With reference to FIGS. 29-31, in certain embodiments, a tissue retrieval system can include an integral cord retention slot 350 formed in the actuator 357 to releasably engage the cord loop 32. As illustrated in FIG. 29, the retention slot 350 can comprise a retention tab 352 and an abutment 354 spaced apart by a gap 356. The relative positions to of the retention tab 352 and the abutment 354 can define a gap 356 sized to releasably engage the cord loop 32. As illustrated, the retention tab can have a wedge-like, tapered profile having a first end 358 a first distance from the abutment and a second end 360 a second distance from the abutment, the second distance larger than the first distance. This wedge-like profile can tend to retain a cord loop between the first end 358 of the retention tab 352 and the abutment 354 until application of a given force to cinch the tissue retrieval bag.

With continued reference to FIGS. 29-31, the actuator 357 of a tissue retrieval system can comprise a receiving channel 359 in which a portion of the cord loop 32 is stored. In the illustrated embodiment, the receiving channel 359 is configured with the retention slot 350 integrally formed therein. With the guide bead 50 positioned adjacent to the actuator 357 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 359 on the actuator 357 can be inserted into the gap 356 between the abutment 354 and the retention tab 352.

In the illustrated embodiments, the cord retention slot 350 prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag.

Figure 32:
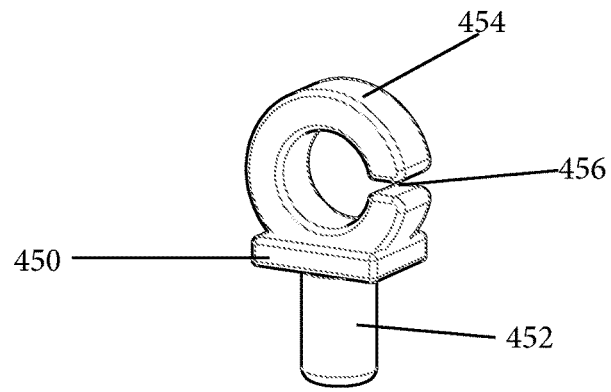
FIG. 32 is a perspective view of an embodiment of a cord retention pin for a tissue retrieval system.
Figure 33:
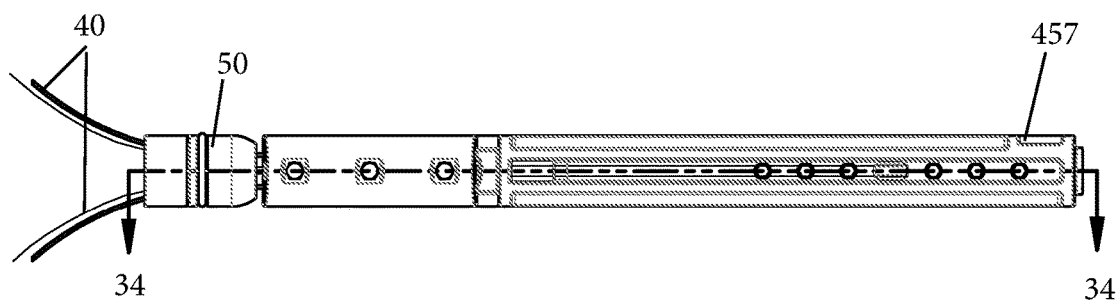
FIG. 33 is a bottom view of an embodiment of tissue retrieval system having the cord retention pin of FIG. 32.
Figure 34:
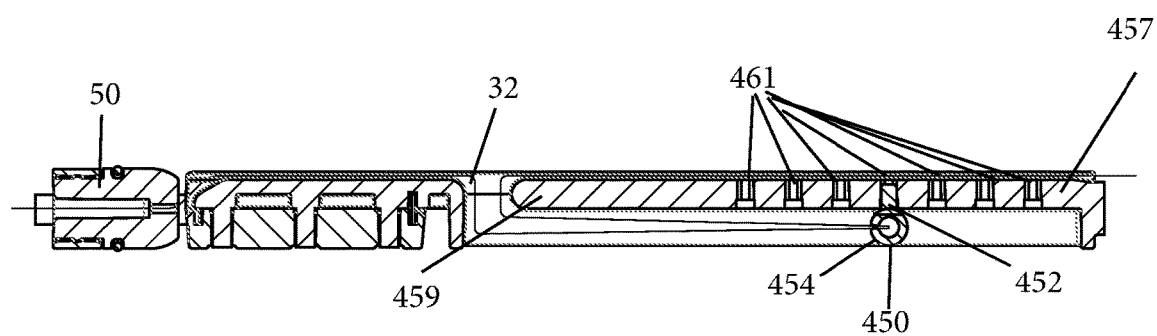
FIG. 34 is a cross sectional side view of the tissue retrieval system of FIG. 33.

With reference to FIGS. 32-34, in certain embodiments, a tissue retrieval system can include a positionable cord retention slot 450 coupled to the actuator 457 to releasably engage the cord loop 32. As illustrated in FIG. 32, the retention slot 450 can comprise a positioning pin 452 and a hoop 454 having a gap or slot 456 formed therein. The gap 456 is sized to releasably engage the cord loop 32.

With continued reference to FIGS. 32-34, the actuator 457 of a tissue retrieval system can comprise a receiving channel 459 in which a portion of the cord loop 32 is stored. In the illustrated embodiment, the receiving channel 459 is configured with a plurality of positioning holes 461 formed therein and longitudinally spaced from one another. In various embodiments, the actuator positioning holes 461 can have circular, hexagonal or other geometric shapes to frictionally engage and retain the positioning pin 452 of the positionable retention slot 450. As the dimensions for the length of the cord loop and the actuator can vary slightly, the degree of tension of the cord loop can also vary. Advantageously, a desired tension can be achieved in the cord loop despite the potential for variation in the length of the cord loop by adjusting the position of the retention slot 450 relative to the actuator through selection of a positioning hole 461. During initial assembly of a tissue retrieval system having a positionable retention slot 450, the stored portion of the cord loop 32 is first attached to the retention slot 450, the cord is then tensioned, and the retention slot 450 is then pressed into the appropriate positioning hole 461 maintaining desired tensioning of the cord loop 32. With the guide bead 50 positioned adjacent to the actuator 457 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 459 on the actuator 457 can be retained by the retention slot 450.

In the illustrated embodiments, the cord retention slot 450 prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag.

Figure 35:
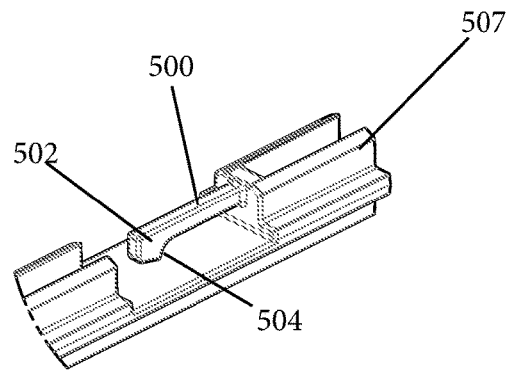
FIG. 35 is a perspective view of an embodiment of actuator having a cord retention hook for a tissue retrieval system.
Figure 36:
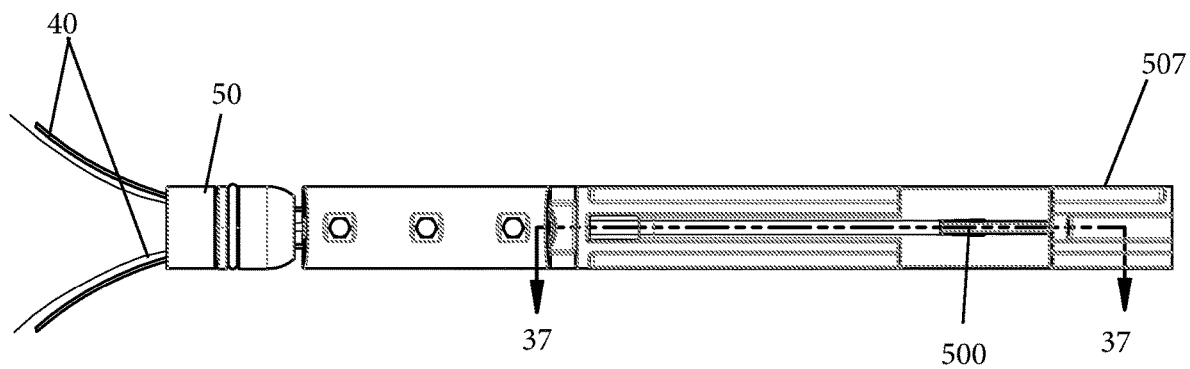
FIG. 36 is a bottom view of an embodiment of tissue retrieval system having the actuator of FIG. 35.
Figure 37:
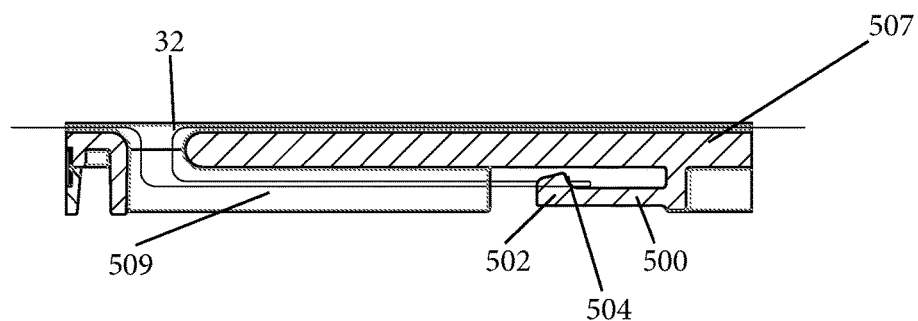
FIG. 37 is cross-sectional side view of the tissue retrieval system of FIG. 36.

With reference to FIGS. 35-37, in certain embodiments, a tissue retrieval system can include an integral cantilever hook 500 formed in the actuator 507 to releasably engage the cord loop 32. As illustrated in FIG. 35, the cantilever hook 500 can comprise a retention tip 502 at an end thereof. The retention tip can have a profile sized and configured to releasably engage the cord loop 32. As illustrated, the retention tab can have a ramped surface 504 about which the cord loop 32 is positioned. This ramped surface retains the cord loop until application of a given force to cinch the tissue retrieval bag tends to advance the cord loop over the ramped surface of the retention tip 502, deflecting the cantilever hook 500.

With continued reference to FIGS. 35-37, the actuator 507 of a tissue retrieval system can comprise a receiving channel 509 in which a portion of the cord loop 32 is stored. In the illustrated embodiment, the receiving channel 509 is configured with the cantilever hook 500 integrally formed therein. With the guide bead 50 positioned adjacent to the actuator 507 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 509 on the actuator 507 can be retained by the retention tip 502 of the cantilever hook 500.

In the illustrated embodiments, the cantilever hook 500 prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag.

While the illustrated embodiment includes an integral cantilever hook, in other embodiments, it is contemplated that a positionable cantilever hook can be coupled to an actuator in a similar manner to that described above with reference to the positionable retention slot of FIGS. 32-34. Advantageously, such a positionable cantilever hook can provide a desired tension in the cord loop 32 despite variations in cord length. The hook can be molded as a separate component and pressed into the receiving channel of an embodiment of actuator. The actuator can include a series of longitudinal positioning holes for installing the hook. The hook can include at least one positioning pin for installation into the actuator positioning holes. The actuator positioning holes can have circular, hexagonal, or other geometric shapes. During initial assembly of a tissue retrieval system having a positionable cantilever hook, the stored portion of the cord loop is first attached to the hook, the cord is then tensioned, and the hook is then pressed into the appropriate positioning holes to maintain a desired tensioning of the cord loop.

Figure 38:
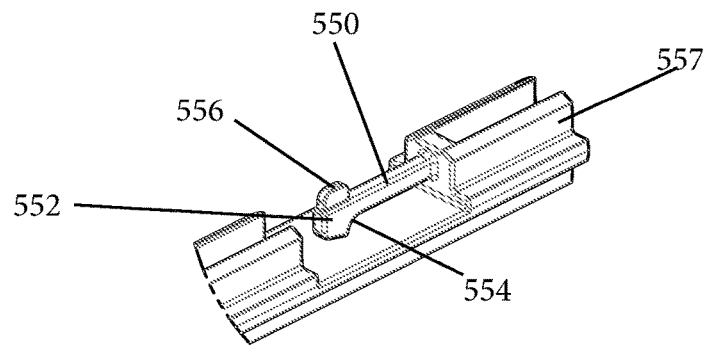
FIG. 38 is a perspective view of an embodiment of actuator having another embodiment of cord retention hook for a tissue retrieval system.
Figure 39:
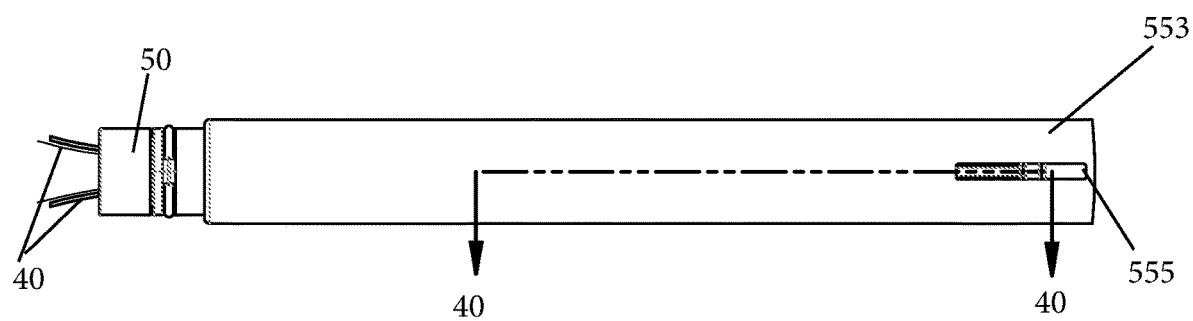
FIG. 39 is a bottom view of a portion of a tissue retrieval system having the actuator of FIG. 38.
Figure 40:
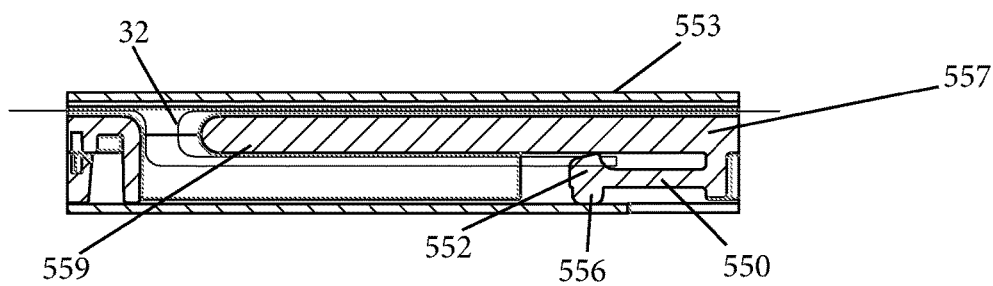
FIG. 40 is a cross sectional side view of the tissue retrieval system of FIG. 39 with the cord retention hook in a retention configuration.
Figure 41:
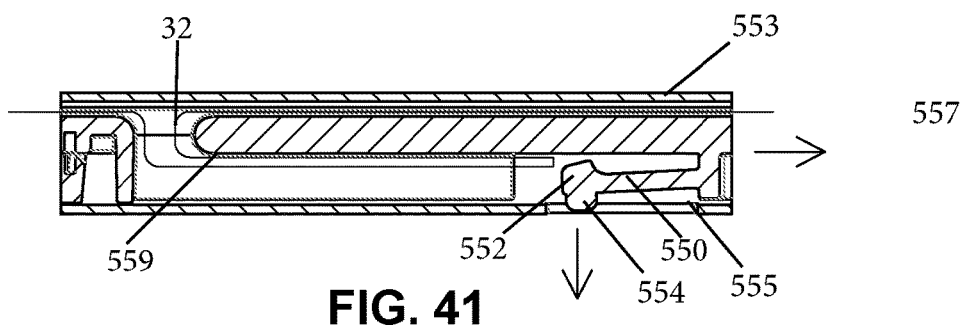
FIG. 41 is a cross sectional side view of the tissue retrieval system of FIG. 39 with the cord retention hook in a released configuration.

With reference to FIGS. 38-41, in certain embodiments, a tissue retrieval system can include an integral cantilever hook 550 formed in the actuator 557 to releasably engage the cord loop 32. As illustrated in FIG. 38, the cantilever hook 550 can comprise a retention tip 552 at an end thereof. The retention tip 552 can have a profile sized and configured to releasably engage the cord loop 32. As illustrated, the retention tab can have a ramped surface 554 about which the cord loop 32 is positioned. The cantilever hook 550 can also have a latch protrusion 556 extending therefrom and engageable with an inner surface of a lumen of introducer tube 553. With the latch protrusion 556 engaged with the inner surface of the lumen of the introducer tube 553, the cantilever hook 550 is maintained in a position to retain the cord loop 32.

With continued reference to FIGS. 38-41, the actuator 557 of a tissue retrieval system can comprise a receiving channel 559 in which a portion of the cord loop 32 is stored. In the illustrated embodiment, the receiving channel 559 is configured with the cantilever hook 550 integrally formed therein. With the guide bead 50 positioned adjacent to the actuator 557 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 559 on the actuator 557 can be retained by the retention tip 552 of the cantilever hook 550.

In the illustrated embodiments, the cantilever hook 550 prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag. As illustrated, the cantilever hook 550 cannot deflect a sufficient distance within the introducer tube 553 to allow release of the cord loop 32 until adequate clearance is provided for the hook to deflect. The clearance can be provided by a mating slot 555 or hole in the introducer tube 553. During cinching of the tissue retrieval bag, the actuator 557 is withdrawn relative to the introducer tube 553, which positions the latch protrusion 556 in the slot 555, allowing deflection of the cantilever hook 550 to allow further movement of the guide bead 50 along the support arms to cinch the tissue retrieval bag.

Figure 42:
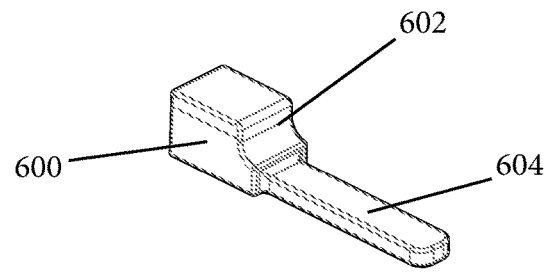
FIG. 42 is a perspective view of an embodiment of cord retention wedge for a tissue retrieval system.
Figure 43:
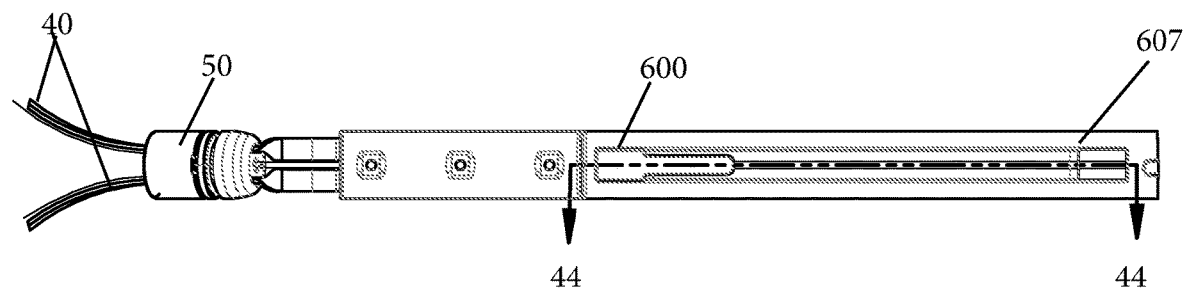
FIG. 43 is a bottom view of an embodiment of tissue retrieval system having the cord retention wedge of FIG. 42.
Figure 44:
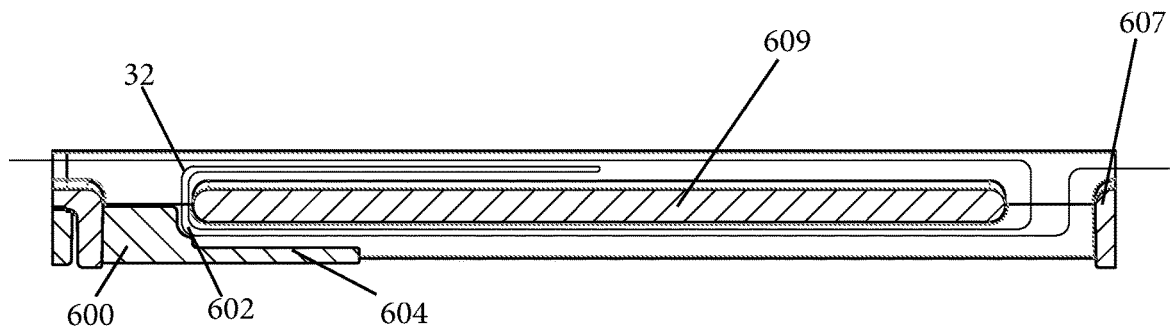
FIG. 44 is a cross sectional side view of the tissue retrieval system of FIG. 43.

With reference to FIGS. 42-44, in certain embodiments, a tissue retrieval system can include a retention wedge 600 disposed in the actuator 607 to frictionally engage the cord loop 32. As illustrated in FIG. 42, the wedge 600 can comprise a molded component having a wedge surface 602 and a guide 604 extending therefrom.

With continued reference to FIGS. 42-44, the actuator 607 of a tissue retrieval system can comprise a receiving channel 609 in which a portion of the cord loop 32 is stored. In the illustrated embodiment, the wedge 600 can be press fit into an opening in the receiving channel 609 to frictionally engage the cord loop 32. With the guide bead 50 positioned adjacent to the actuator 607 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 609 on the actuator 607 can be retained by frictional engagement with the wedge surface 602 of the wedge 600.

In the illustrated embodiments, frictional engagement of the cord loop 32 with the wedge 600 prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag that overcomes the frictional engagement with the wedge 600.

Figure 45:
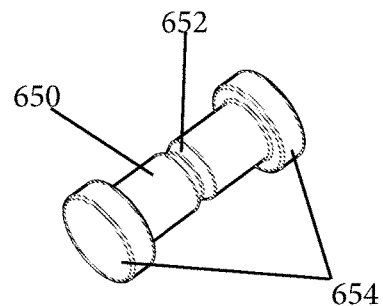
FIG. 45 is a perspective view of an embodiment of frangible pin for a tissue retrieval system.
Figure 46:
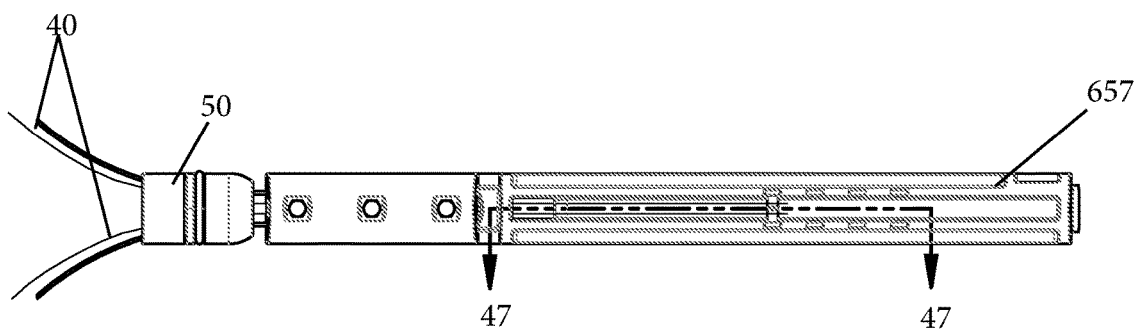
FIG. 46 is a bottom view of an embodiment of tissue retrieval system having the frangible pin of FIG. 45.
Figure 47:
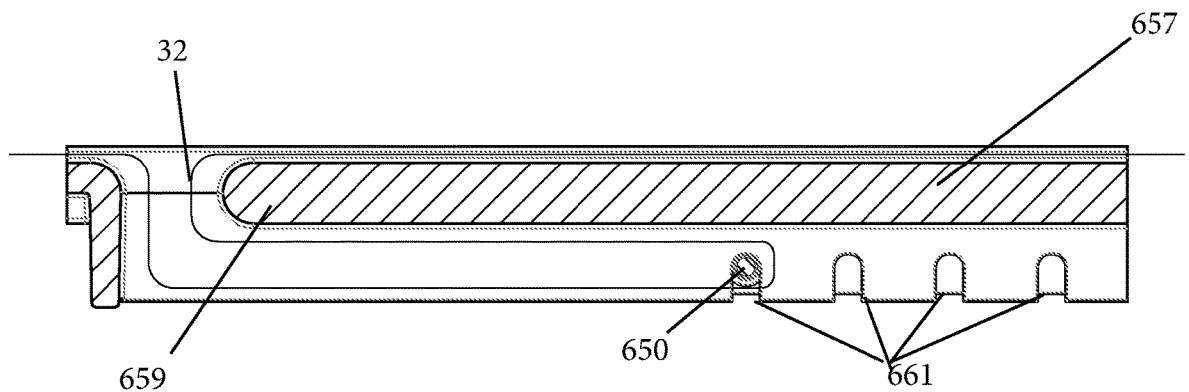
FIG. 47 is a cross sectional side view of the tissue retrieval system of FIG. 46.

With reference to FIGS. 45-47, in certain embodiments, a tissue retrieval system can include a frangible pin 650 disposed in the actuator 657 to releasably engage the cord loop 32. As illustrated in FIG. 45, the pin 650 can comprise a molded generally cylindrical component having a weakened section, such as a necked area or groove 652 and radially protruding flanges 654 or mounts at a first end and a second end thereof.

With continued reference to FIGS. 45-47, the actuator 657 of a tissue retrieval system can comprise a receiving channel 659 in which a portion of the cord loop 32 is stored. In the illustrated embodiment, ends of the stored portion of the cord loop 32 can be placed over the pin 650 and the pin 650 positioned on the actuator 657 in an orientation that is perpendicular to a longitudinal axis of the actuator 657. In some embodiments, the actuator comprises a plurality of holes or slots 661 that are longitudinally spaced from one another. The slots 661 can be sized to receive the pin 650. During initial assembly of the tissue retrieval system, the stored portion of the cord loop 32 is first tensioned and the frangible pin 650 is then inserted into the appropriate slot 661 on the actuator 657 to maintain a desired tensioning of the cord loop 32. With the guide bead 50 positioned adjacent to the actuator 657 such that the guide bead 50 is positioned at a proximal position on the support arms 40 (which corresponds to a stowed or initially deployed, open tissue retrieval bag configuration of a tissue retrieval system as illustrated in FIGS. 1-3), a portion of the cord loop 32 that is stored in the receiving channel 659 on the actuator 657 can be retained by the pin 650.

In the illustrated embodiments, the frangible pin 650 prevents unintentional movement of the guide bead 50 and retrieval bag relative to the support arms 40 by constraining the stored portion of the cord loop 32 and maintaining the remaining cord loop 32 within the introducer tube in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag that fractures the frangible pin 650 and releases the cord loop 32.

Figure 48:
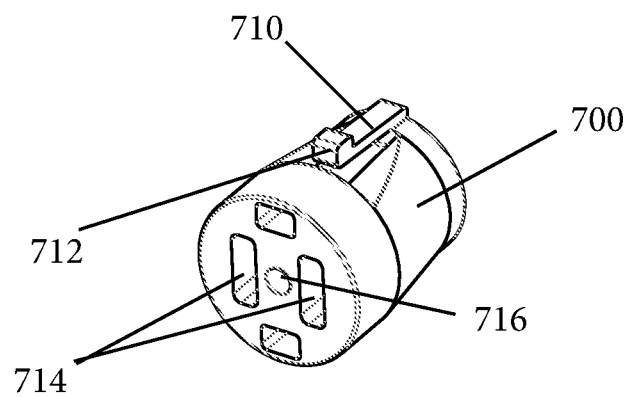
FIG. 48 is a perspective view of a collar for a tissue retrieval system.
Figure 49:
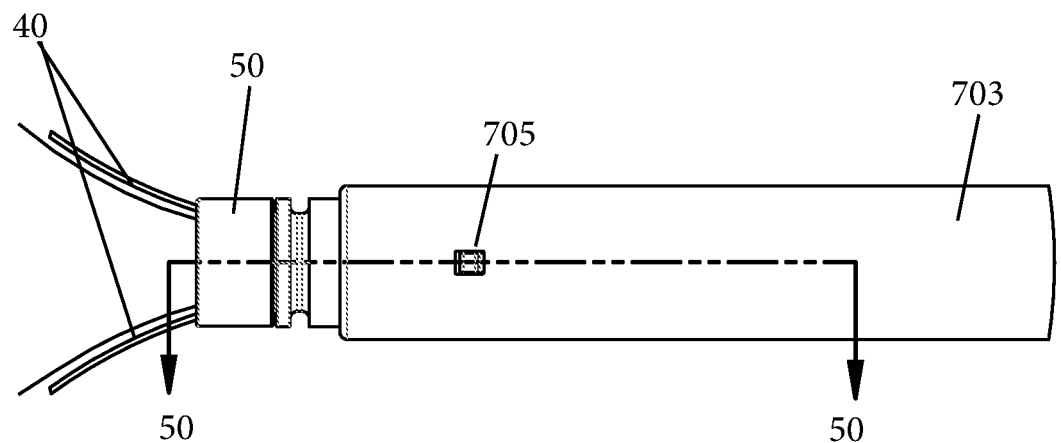
FIG. 49 is a bottom view of an embodiment of tissue retrieval system having the collar of FIG. 48.
Figure 50:
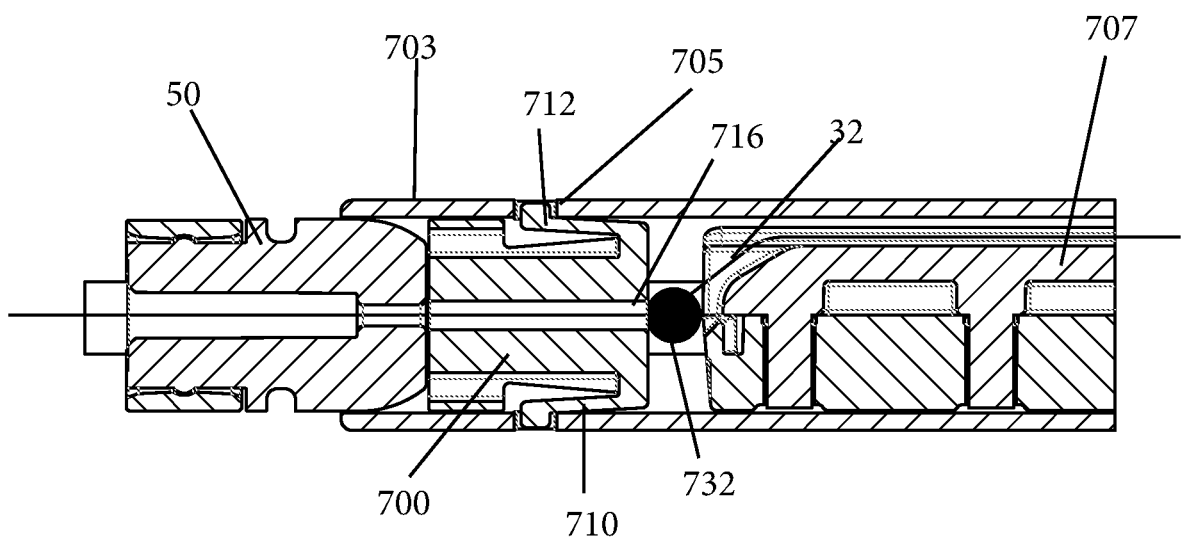
FIG. 50 is a cross sectional side view of the tissue retrieval system of FIG. 49.

With reference to FIGS. 48-50, in certain embodiments, a tissue retrieval system can include an intermediate collar 700 positioned between the actuator 707 and the bead 50. As illustrated in FIG. 48, intermediate collar can comprise at least one cantilever spring arm 710 having a latch tab 712 positioned thereon. For example, the illustrated embodiment of collar 700 has a generally cylindrical body sized to be longitudinally axially slidable within the lumen of the introducer and comprises two cantilever spring arms 710 positioned diametrically opposed to one another with respect to the cylindrical body. As illustrated, the intermediate collar 700 comprises a pair of slots 714 extending therethrough that are sized to slidably receive the support arms of the tissue retrieval system. Additionally, the intermediate collar 700 can comprise a bore 716 sized to receive the cord loop 32 therethrough.

With continued reference to FIGS. 48-50, the cord loop 32 comprises a slip knot 732 tied therein between the actuator 707 and the intermediate collar 700. The slip knot 732 interfaces with the intermediate collar 700. The cord loop 32 is threaded through the bore 716 on the intermediate collar 700. The slip knot 732 is larger than the bore 716 on the intermediate collar 700 and interference between the slip knot 732 and the bore 716 prevents the slip knot 732 from pulling through the bore 716 until the slip knot 732 is untied. The slip knot 732 is positioned proximal to the intermediate collar.

With continued reference to FIGS. 48-50, in embodiments of the tissue retrieval system having an intermediate collar 700, the introducer tube 703 comprises at least one hole or mating slot 705 sized and configured to receive the latch tab 712 of the intermediate collar 700. In the illustrated embodiment, the introducer comprises two mating slots 705 diametrically opposed on the introducer tube 703 to receive the corresponding two latch tabs 712. The mating slots 705 are positioned at a location on the introducer tube 703 corresponding to the intermediate collar having been advanced distally such that the tissue retrieval bag is in an initial deployed, open configuration. As the actuator 707 is advanced and the retrieval bag is deployed, the intermediate collar 700 will advance towards the distal end of the introducer tube 703 and then lock in position with the latch tabs 712 positioned in the mating slots 705. With the retrieval bag fully deployed, the intermediate collar 700 acts as a stop to prevent the slip knot 732 and the cord loop 32 from pulling through the collar 700.

In the illustrated embodiments, the interference of the slip knot 732 with the bore 716 of the intermediate collar 700 prevents unintentional movement of the guide bead 50 and retrieval bag relative to the support arms 40 by maintaining the cord loop 32 distal of the intermediate collar 700 in a tensioned condition. With the cord loop maintained in a tensioned condition, resistance to inadvertent movement of the guide bead 50 retrieval bag is provided while allowing the guide bead 50 and retrieval bag to slide relative to the support arms 40 at a given force during cinching of the retrieval bag that can untie the slip knot 732. The slip knot 732 tail, which is the portion of the knot that unties the slip knot 732 when tensioned, is the proximal end of the cord loop 32 and is attached to the retention slot on the actuator 707. During cinching of the retrieval bag, as the actuator 707 is retracted proximally, the proximal end of the cord loop 32 is tensioned relative to the slip knot 732 causing the slip knot to be untied. Once the retrieval bag is cinched closed, the proximal end of the cord loop 32 can be manually grasped by the surgeon and released from the actuator retention slot.

Figure 51:
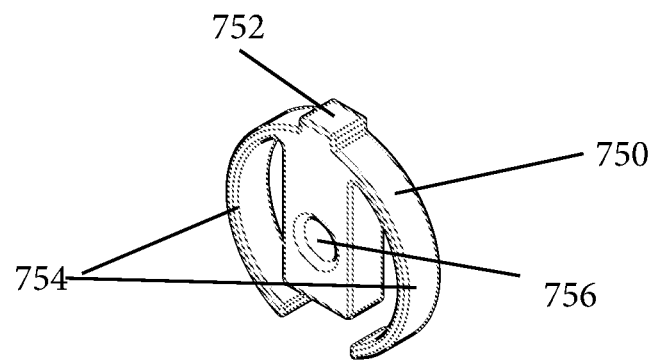
FIG. 51 is a perspective view of a spring clip for a tissue retrieval system.
Figure 52:
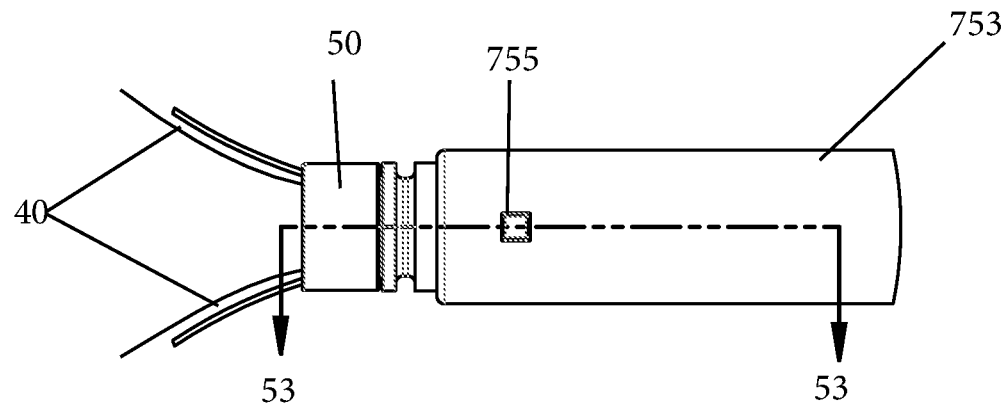
FIG. 52 is a bottom view of an embodiment of tissue retrieval system having the spring clip of FIG. 51.
Figure 53:
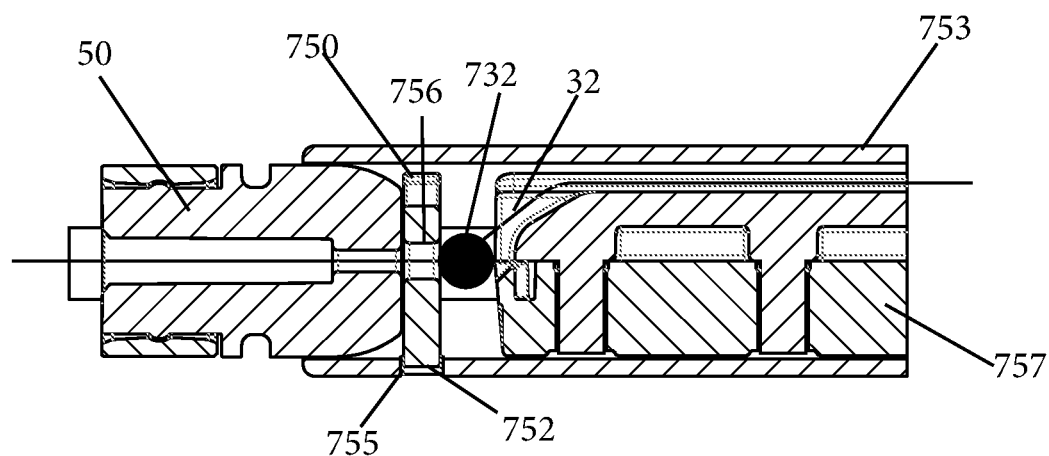
FIG. 53 is a cross sectional side view of the tissue retrieval system of FIG. 52.

With reference to FIGS. 51-53, in certain embodiments, a tissue retrieval system can include an intermediate collar such as a spring clip retaining ring 750 positioned between the actuator 757 and the bead 50. As illustrated in FIG. 51, the retaining ring 750 can comprise at least one spring arm 754 that is biased radially outwardly and a barb 752 positioned thereon. Additionally, the retaining ring can comprise a bore 756 sized to receive the cord loop 32 therethrough.

With continued reference to FIGS. 51-53, the cord loop 32 comprises a slip knot 732 tied therein between the actuator 757 and the retaining ring 750. The slip knot 732 interfaces with the retaining ring 750. The cord loop 32 is threaded through the bore 756 on the retaining ring 750. The slip knot 732 is larger than the bore 756 on the retaining ring 750 and interference between the slip knot 732 and the bore 756 prevents the slip knot 732 from pulling through the bore 756 until the slip knot 732 is untied. The slip knot 732 is positioned proximal to the retaining ring.

With continued reference to FIGS. 51-53, in embodiments of the tissue retrieval system having a retaining ring 750, the introducer 753 comprises at least one hole or mating slot 755 sized and configured to receive the barb 752 of the retaining ring 750. The mating slot 755 is positioned at a location on the introducer 753 corresponding to the intermediate collar having been advanced distally such that the tissue retrieval bag is in an initial deployed, open configuration. As the actuator 757 is advanced and the retrieval bag is deployed, the retaining ring 750 will advance towards the distal end of the introducer tube 753 and then the bias of the spring arms 754 will lock the retaining ring 750 in position with the barb 752 positioned in the mating slot 755. With the retrieval bag fully deployed, the retaining ring 750 acts as a stop to prevent the slip knot 732 and the cord loop 32 from pulling through the retaining ring 750.

In the illustrated embodiments, the interference of the slip knot 732 with the bore 756 of the retaining ring 750 prevents unintentional movement of the guide bead 50 and retrieval bag relative to the support arms 40 by maintaining the cord loop 32 distal of the retaining ring 750 in a tensioned condition. With the cord loop maintained in a tensioned condition, resistance to inadvertent movement of the guide bead 50 and retrieval bag is provided while allowing the guide bead 50 and retrieval bag to slide relative to the support arms 40 at a given force during cinching of the retrieval bag that can untie the slip knot 732. The slip knot 732 tail, which is the portion of the knot that unties the slip knot 732 when tensioned, is the proximal end of the cord loop 32 and is attached to the retention slot on the actuator 757. During cinching of the retrieval bag, as the actuator 757 is retracted proximally, the proximal end of the cord loop 32 is tensioned relative to the slip knot 732 causing the slip knot to be untied. Once the retrieval bag is cinched closed, the proximal end of the cord loop 32 can be manually grasped by the surgeon and released from the actuator retention slot.

Figure 54:
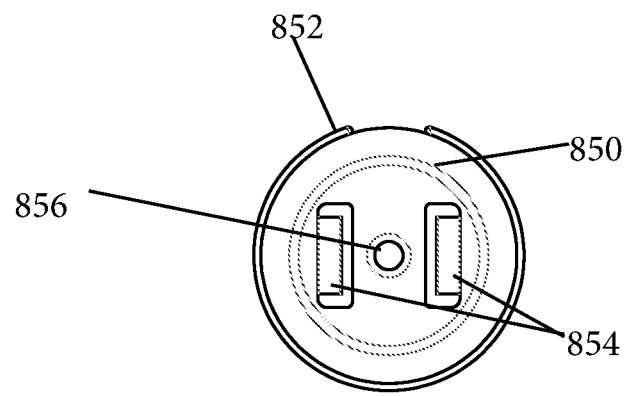
FIG. 54 is a front view of an embodiment of guide bead for a tissue retrieval system.
Figure 55:
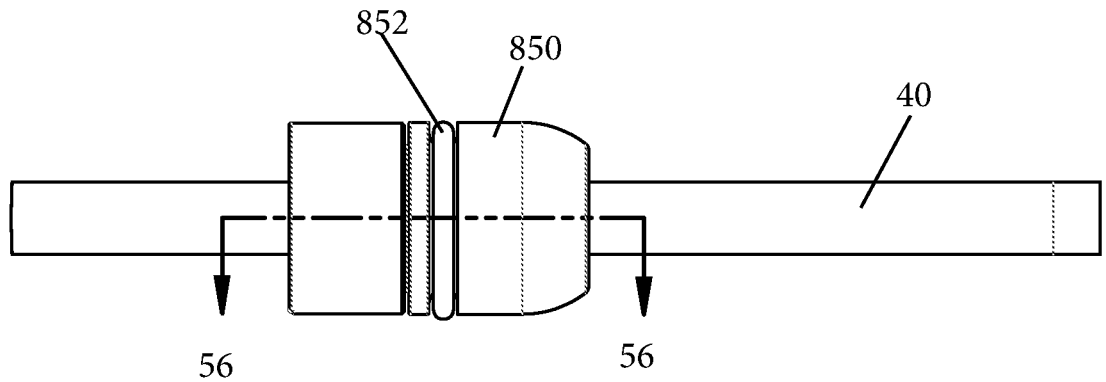
FIG. 55 is a side view of the guide bead of FIG. 54 disposed on support arms of an embodiment of tissue retrieval system.
Figure 56:
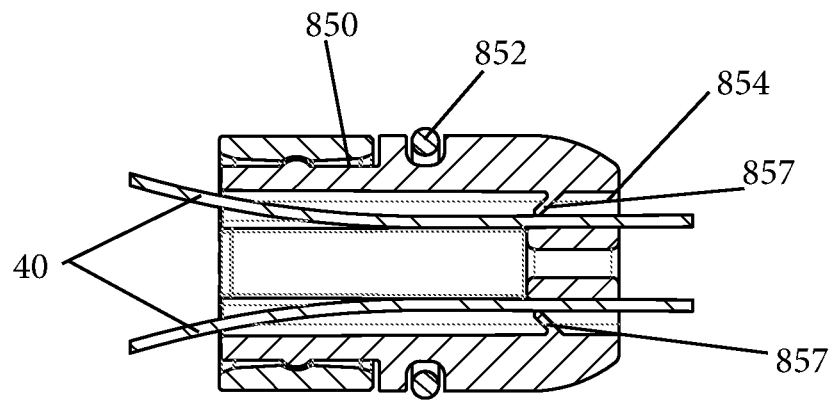
FIG. 56 is a cross sectional top view of the guide bead and support arms of FIG. 55.

With reference to FIGS. 54-56, certain aspects of an embodiment of tissue retrieval system including a bead that frictionally engages support arms are illustrated. The guide bead 850 of the tissue retrieval system can comprise slots 854 sized and configured to receive support arms 40 and a bore 856 or passage sized and configured to receive a cord loop. Additionally, the guide bead 850 can comprise a snap ring 852 that can be compressed to allow the bead 850 to be positioned in the introducer when the tissue retrieval bag is stowed, but is biased to expand to a larger diameter profile upon deployment of the tissue retrieval bag to prevent reentry of the guide bead in the introducer. In other embodiments, the guide bead 850 does not include a snap ring 852 and bunching of the tissue retrieval bag at a distal end of the introducer during cinching can maintain a position of the bead 850 relative to the introducer to facilitate cinching of the tissue retrieval bag.

With continued reference to FIGS. 54-56, the bead 850 of the tissue retrieval system is configured to frictionally engage the support arms to reduce the potential for inadvertent movement of the guide bead and tissue retrieval bag relative to the support arms. For example, the bead 850 can include an integral directional finger element 857 within each of the support arm slots 854. The finger elements 857 can be sized and configured to frictionally engage the support arms 40 to prevent the bead 850 and retrieval bag from inadvertently sliding on the support arms. The finger elements 857 can allow the support arms 40 to easily slide through the slots 854 during assembly of the retrieval system and will prevent unintentional movement of the bead and retrieval bag. As illustrated, the finger elements 857 extend at an angle transverse to the longitudinal axis of the slots 854 that provide barb-like frictional engagement with the support arms 40, tending to resist movement of the bead 850 relative to the support arms in a first direction while allowing movement of the bead 850 relative to the support arms in a second direction opposite to the first direction. The finger elements 857 allow the support arms 40 to slide relative to the bead 850 at a given force during cinching of the retrieval bag. In certain embodiments, the bead can be molded in two halves and snap fit together. This two-piece bead would allow the molding of multiple directional finger elements 857 within each slot 854. Thus, while the illustrated embodiment includes a finger element 857 positioned in each slot 854, it is contemplated that in other embodiments, each slot 854 can comprise a plurality of finger elements 857. In still other embodiments, only one of the slots 854 can comprise a finger element 857.

While various embodiments of actuator and guide bead are illustrated that maintain tension in a portion of the cord loop to prevent inadvertent movement of the guide bead relative to the support arms, it is contemplated that in other embodiments, a portion of the cord loop that is positioned near the distal end of the actuator can be releasably welded or bonded to the actuator to provide resistance to inadvertent movement of the bead and the retrieval bag, but allow the cord to release from the actuator allowing the bead to slide relative to the support arms during cinching of the retrieval bag. In various embodiments, the cord can be ultrasonically welded, thermally welded, or adhesively bonded to the actuator. In other embodiments, the portion of the cord loop that is positioned near the distal end of the actuator can be folded over and releasably trapped or pinched between the actuator cap and the actuator to provide resistance to inadvertent movement of the bead and the retrieval bag. In this case, a small portion of the cord loop would be folded over and pressed between the actuator cap and the actuator during assembly and would release at a given force during cinching of the retrieval bag.

Figure 57:
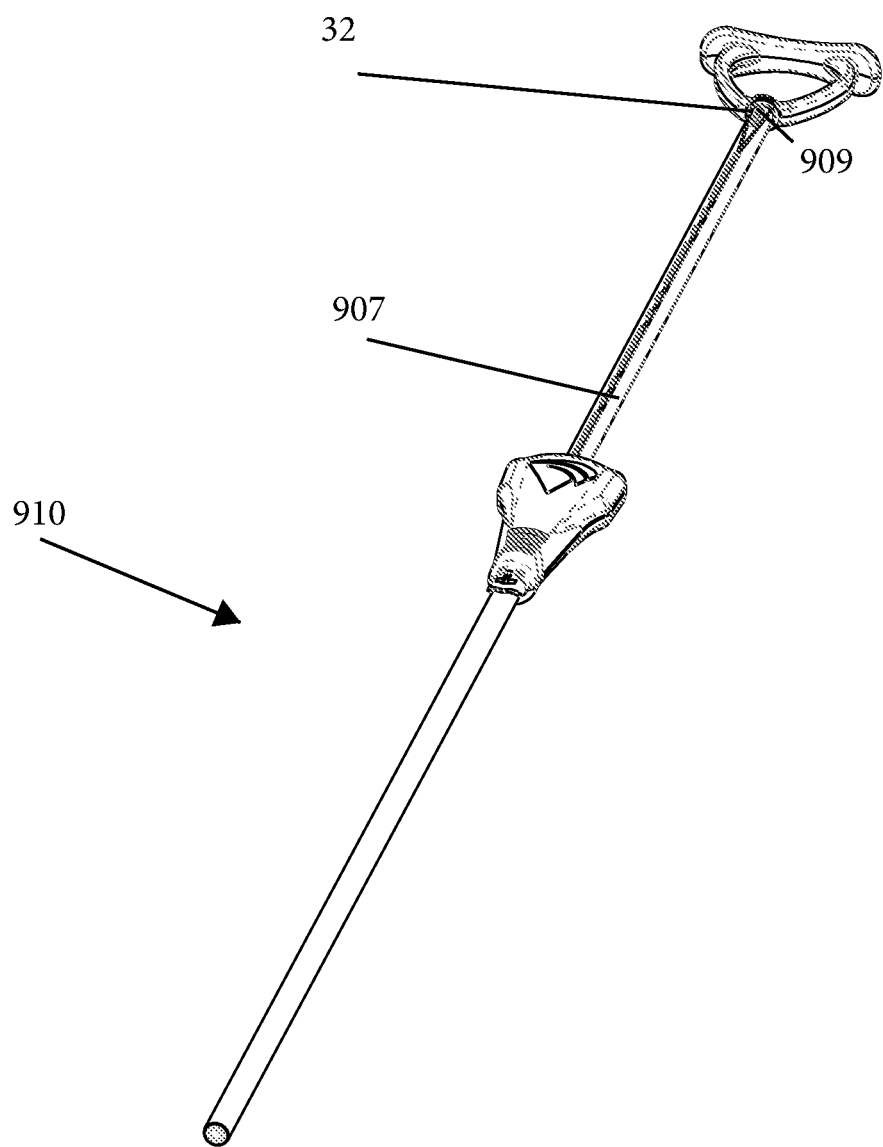
FIG. 57 is a perspective view of another embodiment of tissue retrieval system.
Figure 58:
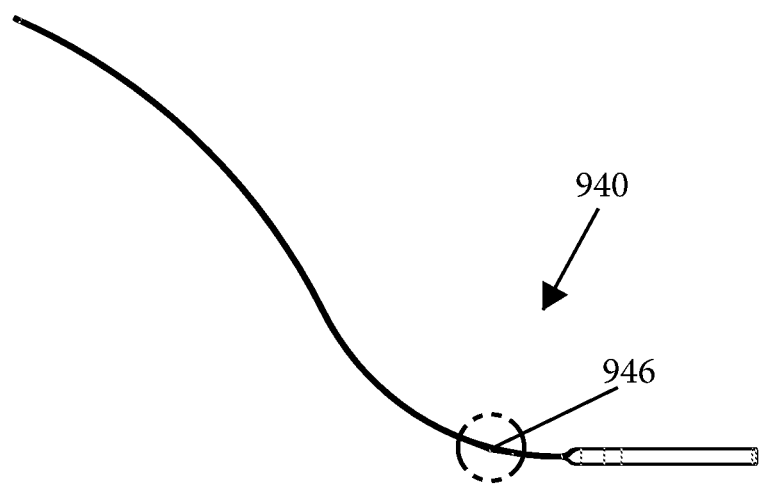
FIG. 58 is a top view of an embodiment of support arm for a tissue retrieval system.
Figure 59:
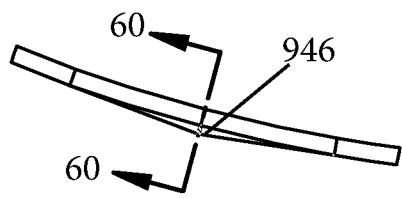
FIG. 59 is a detail view of a retention segment of an embodiment of support arm.
Figure 60:
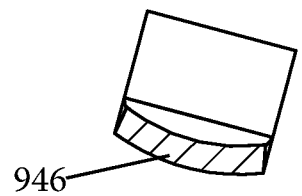
FIG. 60 is a cross sectional front view of the retention segment of FIG. 59.

With reference to FIG. 57, in some embodiments of tissue retrieval system 910, the cord loop 32 can be maintained by a slot 909 formed in the actuator 907. In certain embodiments, the cord loop 32 can be relatively long such that the slot 909 is positioned on or adjacent the handle of the actuator 907. The cord loop 32 can be releasably attached to the slot 909 adjacent handle of the actuator. With the cord loop 32 attached to the retaining slot 909 on the actuator handle, the cord loop would not have any slack and would have minimal to no tension. Once the retrieval bag is deployed by advancing the actuator 907 distally, if an axial force along the longitudinal axis of the device is applied to the retrieval bag, the cord loop 32 would become tensioned to prevent the retrieval bag from inadvertently sliding relative to the support arms. Once the tissue specimen is placed in the retrieval bag, the actuator 907 would be retracted proximally to withdraw the support arms through the bead, cinch the retrieval bag, and fully tension the cord loop. The cord loop 32 can then be detached from the retaining slot 909 on the actuator 907 handle to allow the device and the trocar to be withdrawn from the patient, leaving the retrieval bag in the body cavity and the cord loop 32 disposed across the abdominal wall for subsequent removal of the retrieval bag from the patient. In other embodiments, the cord loop can be attached to an intermediate portion of the actuator rather than the handle. In this case, the cord loop length can be relatively short relative to the illustrated embodiment such that with the cord loop in a retaining slot disposed at an intermediate portion of the actuator between the proximal end and the distal end, the cord loop has no slack and minimal tension.

With reference to FIGS. 58-67, in certain embodiments of tissue retrieval system, the support arms can be configured to generate a desired resistance to inadvertent movement of the tissue retrieval bag with profiles other than the dimples or domes described with respect to the embodiments of FIGS. 5-12. For example, in some embodiments, the support arms 940 can include a semicircular or C curled configuration 946 at one or more sections distal to the interface with the slots on the bead with the bead positioned with the tissue retrieval bag in a stowed or initially deployed configuration (FIGS. 1-3) to provide resistance to inadvertent movement of the bead. This semicircular configuration would be sized and configured to allow the support arms to be pulled through the slots in the bead at a given force.

Figure 61:
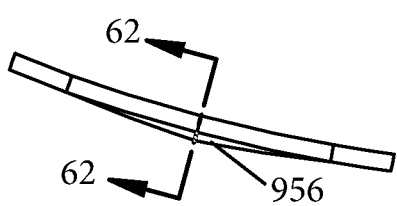
FIG. 61 is a detail view of another embodiment of retention segment of an embodiment of support arm.
Figure 62:
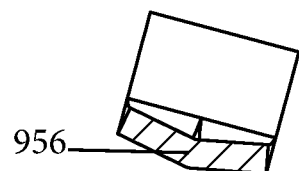
FIG. 62 is a cross sectional front view of the retention segment of FIG. 61.

With reference to FIGS. 61-62, in other embodiments, the support arms 940 can comprise a region formed into folded, crimped, or slight V configurations 956 with axial bends at sections distal to the interface with the slots on the bead positioned with the tissue retrieval bag in a stowed or initially deployed configuration (FIGS. 1-3) to provide resistance to inadvertent movement of the bead.

Figure 63:
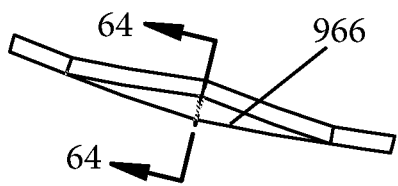
FIG. 63 is a detail view of another embodiment of retention segment of an embodiment of support arm.
Figure 64:
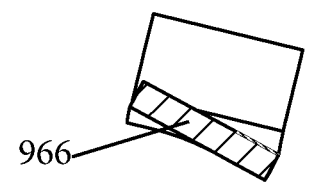
FIG. 64 is a cross sectional front view of the retention segment of FIG. 63.

With reference to FIGS. 63-64, in other embodiments, the support arms 940 can comprise a region including slight twists 966 relative to a longitudinal axis of the support arms positioned at sections distal to the interface with the slots on the bead positioned with the tissue retrieval bag in a stowed or initially deployed configuration (FIGS. 1-3). The twists 966 would provide resistance to inadvertent movement of the bead. While certain embodiments of support arms have been illustrated with features that resist inadvertent sliding of the bead, in other embodiments, it is contemplated that other geometric features can be formed into the support arms to resist inadvertent movement of the bead. For example, rather than the illustrated C curl configuration, V configuration, or twist, in some embodiments the support arms can include embossments of various shapes positioned distal to the interface with the slots on the bead including rectangular or oval embossments.

Figure 65:
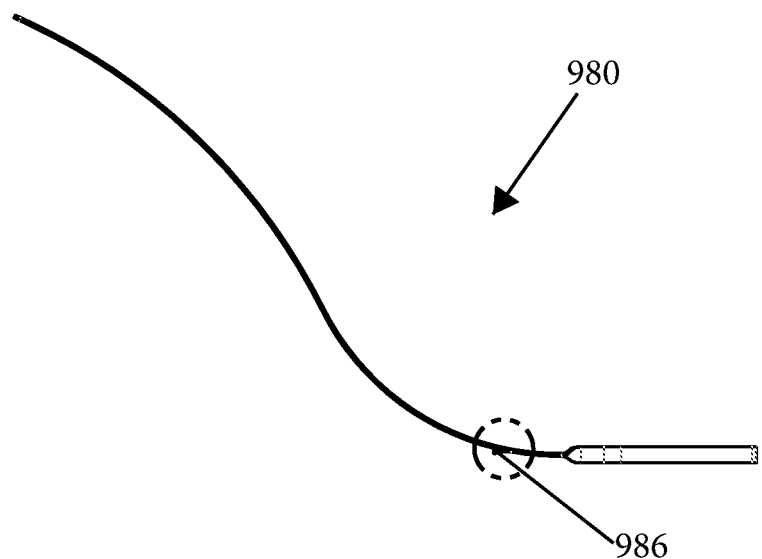
FIG. 65 is a top view of an embodiment of support arm for a tissue retrieval system.
Figure 66:
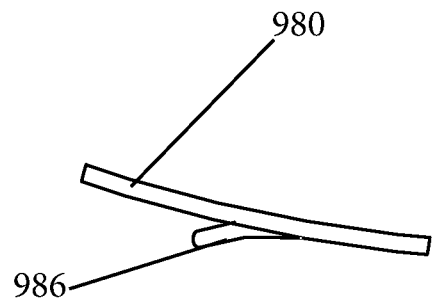
FIG. 66 is a detail view of a retention segment of an embodiment of support arm.
Figure 67:
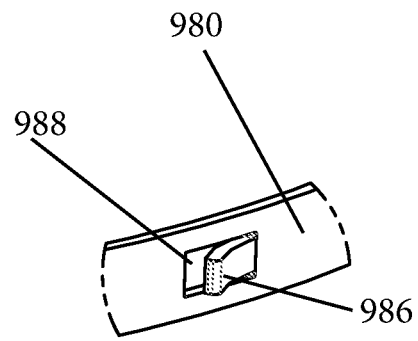
FIG. 67 is a perspective view of the retention segment of FIG. 66.

With reference to FIGS. 65-67, in other embodiments, the support arms 980 can comprise a region comprising an integrally formed cantilever leaf spring 986. The cantilever leaf spring 986 can be formed of a partially cut slot 988 in the support arm 980 such that the leaf spring has a generally rectangular shape with three free edges separated from an adjoining portion of the support arm and one connected edge. The leaf spring 986 can be bent or curled relative to the support arm. The support arms could include integral cantilever leaf springs positioned distal to the interface with the slots on the bead that are designed to provide resistance to inadvertent movement of the bead.

Although this application discloses certain preferred embodiments and examples, it will be understood by those skilled in the art that the present inventions extend beyond the specifically disclosed embodiments to other alternative embodiments and/or uses of the inventions and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims that follow.

What is claimed is:

1. A tissue retrieval system comprising:
   a tubular introducer having a proximal end and a distal end and a lumen extending between the proximal end and the distal end;
   an actuator longitudinally slidable within the lumen of the introducer, the actuator having a proximal end and a distal end;
   a pair of support arms extending from the distal end of the actuator;
   a guide bead, wherein the guide bead comprises a pair of slots extending therethrough, each slot from the pair of slots slidingly receiving a corresponding support arm of the pair of support arms;
   a tissue retrieval bag coupled to the guide bead and removably coupled to the support arms, the tissue retrieval bag positionable within the lumen of the introducer in a stowed configuration and deployable by longitudinal movement of the actuator within the lumen of the introducer to an open configuration wherein the tissue retrieval bag is suspended from the support arms;
   wherein the support arms comprise at least one retention dome sized and configured to maintain a position of the tissue retrieval bag relative to the support arms; and
   wherein each slot has a first width and the support arms at the at least one retention dome have a second width larger than the first width.

2. The tissue retrieval system of claim 1, wherein the first width is approximately 0.024 inches and the second width is approximately 0.021 inches.

3. The tissue retrieval system of claim 1, wherein a difference between the first width and the second width is approximately 0.003 inches.

4. The tissue retrieval system of claim 1, wherein the at least one retention dome is positioned at a location on the support arm such that the guide bead is proximal the retention dome with the tissue retrieval bag suspended from the support arms.

5. The tissue retrieval system of claim 1, wherein application of a predetermined withdrawal force to the actuator withdraws the support arms relative to the tissue retrieval bag.

6. The tissue retrieval system of claim 5, wherein the predetermined withdrawal force is approximately 4 pounds.

7. The tissue retrieval system of claim 1, wherein the support arms each comprise a first side and a second side opposite the first side, wherein the at least one retention dome is positioned on the first side, and wherein the support arms further comprise an at least one recess on the second side corresponding to the at least one retention dome.

8. The tissue retrieval system of claim 1, wherein the guide bead comprises an assembly having a first portion and a second portion snap fit to the first portion.

9. The tissue retrieval system of claim 8, wherein a portion of the tissue retrieval bag is positioned between and engaged by the first portion and the second portion.

10. The tissue retrieval system of claim 1, wherein the guide bead is formed of a polycarbonate material and the slots deform upon engagement with the at least one retention dome.

11. The tissue retrieval system of claim 1, wherein the at least one retention dome protrudes radially inwardly from the support arms with respect to the lumen of the introducer with the tissue retrieval bag in the stowed configuration.

* * * * *